US012324883B2

(12) United States Patent
Traxler et al.

(10) Patent No.: US 12,324,883 B2
(45) Date of Patent: Jun. 10, 2025

(54) EXPANDABLE BALLOON SHEATHS

(71) Applicant: Medtronic Vascular, Inc., Santa Rosa, CA (US)

(72) Inventors: John Wilson Traxler, Healdsburg, CA (US); Michael Baldwin, Santa Rosa, CA (US); Joseph Duffy, Petaluma, CA (US); John Kantor, Healdsburg, CA (US); Tony Le, Rohnert Park, CA (US); Asim Malik, Windsor, CA (US); Susan Peterson, Santa Rosa, CA (US); Emily Schoenhoff, Santa Rosa, CA (US); Eric Hallberg, Becker, MN (US); Steven Holt, Crystal, MN (US); Erik Svensson, New Hope, MN (US); Ronan Cleary, Galway (IE); Sameer Singh, Santa Rosa, CA (US); Steven Holmgren, Maple Grove, MN (US); Janet Komatsu, San Francisco, CA (US); Traci Colgan, Healdsburg, CA (US); Gregory Hopper, Brooklyn Park, MN (US); Marcel Fuhrer, Healdsburg, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 927 days.

(21) Appl. No.: 15/930,974

(22) Filed: May 13, 2020

(65) Prior Publication Data

US 2020/0269013 A1    Aug. 27, 2020

Related U.S. Application Data

(62) Division of application No. 15/875,343, filed on Jan. 19, 2018, now Pat. No. 10,702,673.

(51) Int. Cl.
*A61M 25/00* (2006.01)
*A61M 25/06* (2006.01)
*A61M 25/10* (2013.01)

(52) U.S. Cl.
CPC .... *A61M 25/0043* (2013.01); *A61M 25/0668* (2013.01); *A61M 25/10* (2013.01);
(Continued)

(58) Field of Classification Search
CPC .. A61M 2025/0024; A61M 2025/1081; A61M 25/0026; A61M 25/0074;
(Continued)

(56) References Cited

U.S. PATENT DOCUMENTS 4,596,559 A * 6/1986 Fleischhacker ... A61M 25/0668
604/161
5,104,388 A * 4/1992 Quackenbush ... A61M 25/0668
604/164.05
(Continued)

FOREIGN PATENT DOCUMENTS

CN    200942233 Y  *  9/2007  ........ A61M 25/0668
JP    2004357847 A  * 12/2004

OTHER PUBLICATIONS

Prosecution History from U.S. Appl. No. 15/875,343, dated Aug. 8, 2019 through Apr. 1, 2020, 42 pp.
(Continued)

*Primary Examiner* — Scott J Medway
(74) *Attorney, Agent, or Firm* — Shumaker & Sieffert, P.A.

(57) ABSTRACT

A tubular sheath for enclosing an expandable balloon attached to the distal portion of a catheter encloses and protects the expandable balloon. The tubular sheath is configured to be slidable and removable from the catheter. The tubular sheath may include a longitudinal splitting element
(Continued)

that is removable as a result of a force applied to the longitudinal splitting element. The longitudinal splitting element is configured to split the wall of the tubular sheath in response to the force. Alternatively, the tubular sheath may include a gripping portion that has relatively poor cohesive strength to adjacent portions of the tubular sheath. The tubular sheath is configured to be removable in response to a force applied to the gripping portion.

20 Claims, 9 Drawing Sheets

(52) U.S. Cl.
CPC ..... *A61M 25/104* (2013.01); *A61M 2025/105* (2013.01); *A61M 2025/1081* (2013.01)
(58) Field of Classification Search
CPC .......... A61M 25/0662; A61M 25/1025; A61M 2025/0046; A61M 2025/105; A61M 25/0668; A61M 25/10; A61M 2025/0681
See application file for complete search history.

(56) References Cited

U.S. PATENT DOCUMENTS

| | | | |
|---|---|---|---|
| 5,188,605 A | 2/1993 | Sleep | |
| 5,263,932 A * | 11/1993 | Jang | A61M 25/104 604/913 |
| 5,383,928 A | 1/1995 | Scott et al. | |
| 5,397,311 A * | 3/1995 | Walker | A61M 25/0668 604/160 |
| 5,639,276 A * | 6/1997 | Weinstock | A61N 1/372 606/129 |
| 5,647,857 A | 7/1997 | Anderson et al. | |
| 5,752,937 A | 5/1998 | Otten et al. | |
| 5,868,719 A | 2/1999 | Tsukernik | |
| 5,893,868 A * | 4/1999 | Hanson | A61F 2/0095 606/198 |
| 5,919,160 A * | 7/1999 | Sanfilippo, II | A61M 39/0208 604/93.01 |
| 5,964,730 A | 10/1999 | Williams et al. | |
| 6,090,135 A * | 7/2000 | Plaia | A61F 2/07 623/1.1 |
| 6,110,146 A | 8/2000 | Berthiaume et al. | |
| 6,122,552 A * | 9/2000 | Tockman | A61M 25/10 607/116 |
| 6,132,450 A * | 10/2000 | Hanson | A61M 25/104 606/198 |
| 6,193,691 B1 * | 2/2001 | Beardsley | A61M 25/0102 604/164.01 |
| 6,254,610 B1 * | 7/2001 | Darvish | A61B 17/22 606/1 |
| 6,478,813 B1 * | 11/2002 | Keith | A61F 2/954 623/1.13 |
| 6,592,548 B2 | 7/2003 | Jayaraman | |
| 6,749,584 B2 * | 6/2004 | Briggs | A61M 25/104 604/103.05 |
| 6,783,542 B2 * | 8/2004 | Eidenschink | A61F 2/958 606/108 |
| 6,805,703 B2 * | 10/2004 | McMorrow | A61F 2/95 623/1.46 |
| 6,939,327 B2 * | 9/2005 | Hall | A61M 25/0668 604/164.05 |
| 7,105,013 B2 | 9/2006 | Durcan | |
| 7,637,893 B2 * | 12/2009 | Christensen | A61B 17/3415 137/849 |
| 7,837,671 B2 * | 11/2010 | Eversull | A61M 25/0668 604/524 |
| 8,414,528 B2 * | 4/2013 | Liu | A61F 2/962 604/103.05 |
| 8,852,257 B2 | 10/2014 | Liu et al. | |
| 9,072,590 B2 | 7/2015 | Wang et al. | |
| 9,119,741 B2 | 9/2015 | Liu et al. | |
| 11,793,977 B2 * | 10/2023 | Korkuch | A61M 60/13 |
| 2001/0049499 A1 * | 12/2001 | Lui | A61M 39/06 604/167.04 |
| 2002/0120324 A1 * | 8/2002 | Holman | A61M 25/104 623/1.11 |
| 2004/0093005 A1 | 5/2004 | Durcan | |
| 2006/0015171 A1 | 1/2006 | Armstrong | |
| 2006/0058866 A1 | 3/2006 | Cully et al. | |
| 2009/0105686 A1 | 4/2009 | Snow et al. | |
| 2009/0221965 A1 * | 9/2009 | Osypka | A61M 25/0662 604/160 |
| 2010/0069852 A1 | 3/2010 | Kelley | |
| 2011/0184509 A1 | 7/2011 | Von Oepen et al. | |
| 2011/0208284 A1 | 8/2011 | Hofmann et al. | |
| 2011/0208292 A1 * | 8/2011 | Von Oepen | A61F 2/97 623/1.23 |
| 2011/0270226 A1 | 11/2011 | Kocur et al. | |
| 2012/0296313 A1 | 11/2012 | Andreacchi et al. | |
| 2013/0018309 A1 | 1/2013 | Ewing et al. | |
| 2014/0343593 A1 | 11/2014 | Chin et al. | |
| 2014/0379065 A1 | 12/2014 | Johnson et al. | |
| 2015/0088241 A1 | 3/2015 | Liu et al. | |
| 2015/0190618 A1 | 7/2015 | Kantor | |
| 2015/0201963 A1 * | 7/2015 | Snow | A61B 10/0233 604/167.03 |
| 2015/0224282 A1 * | 8/2015 | Christiansen | A61M 25/0023 604/164.01 |
| 2015/0328028 A1 | 11/2015 | Wang et al. | |
| 2016/0058983 A1 | 3/2016 | Poker et al. | |
| 2017/0304595 A1 * | 10/2017 | Nagasrinivasa | A61M 25/10 |
| 2018/0043138 A1 | 2/2018 | Chu | |
| 2019/0224448 A1 | 7/2019 | Connors et al. | |
| 2019/0224449 A1 | 7/2019 | Traxler et al. | |
| 2019/0224458 A1 | 7/2019 | Morero et al. | |
| 2019/0224459 A1 | 7/2019 | Pedroni | |
| 2019/0224460 A1 | 7/2019 | Kantor et al. | |

OTHER PUBLICATIONS

Prosecution History from U.S. Appl. No. 15/875,356, dated Aug. 8, 2019 through Feb. 12, 2020, 39 pp.

* cited by examiner

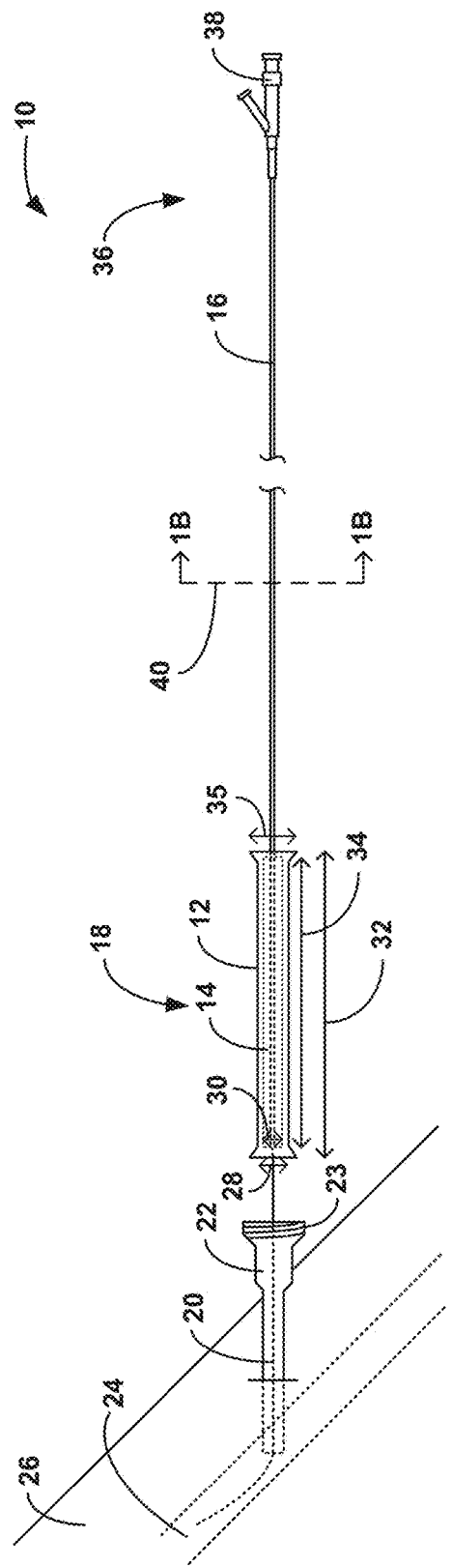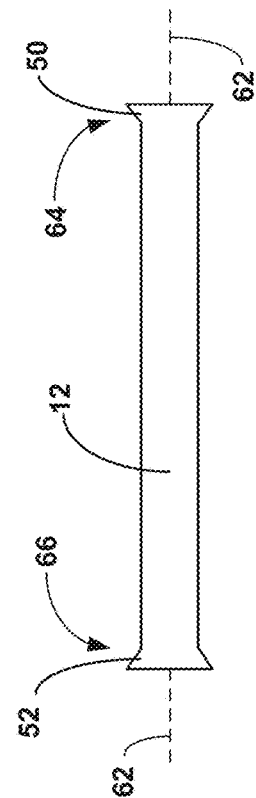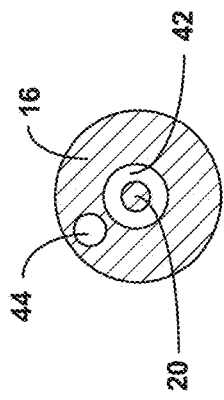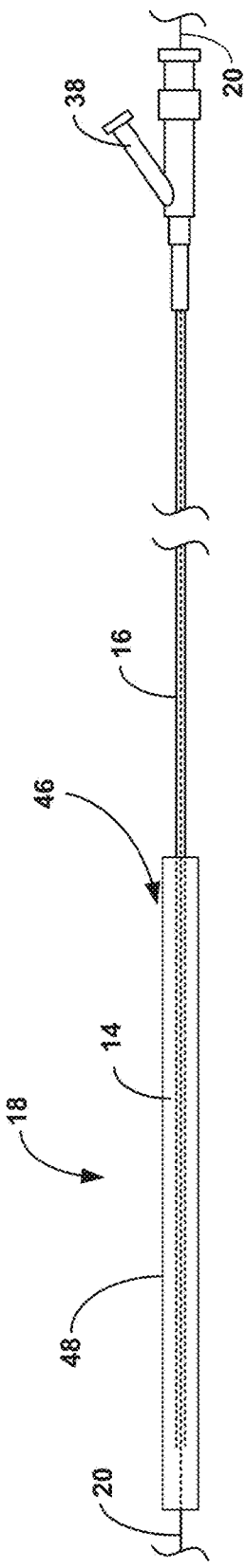
FIG. 1A
FIG. 1B
FIG. 1C
FIG. 1D

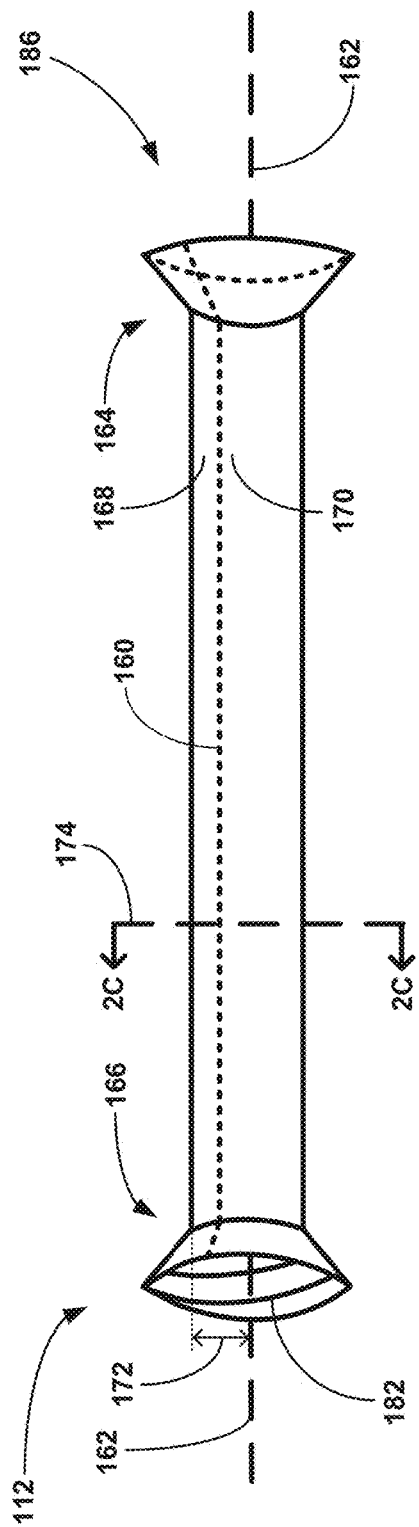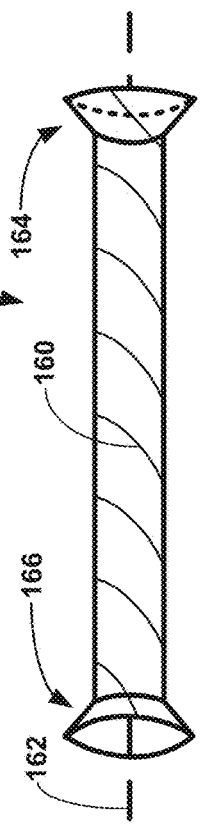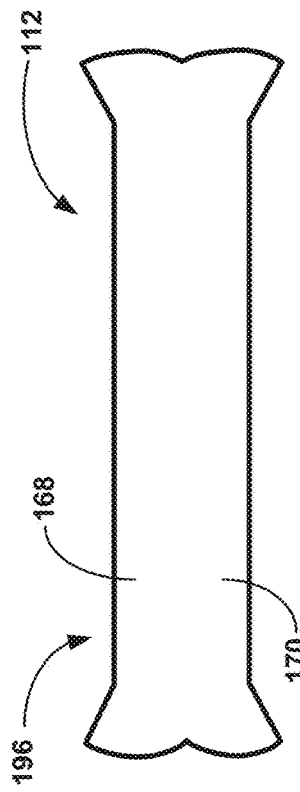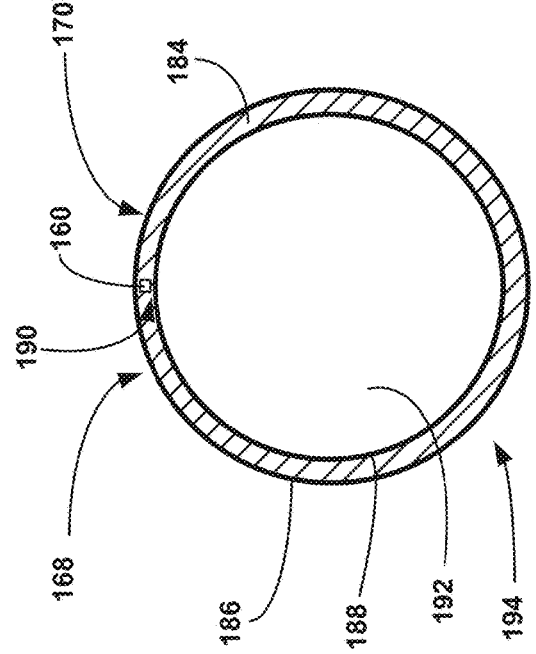
FIG. 2A
FIG. 2B
FIG. 2C
FIG. 2D

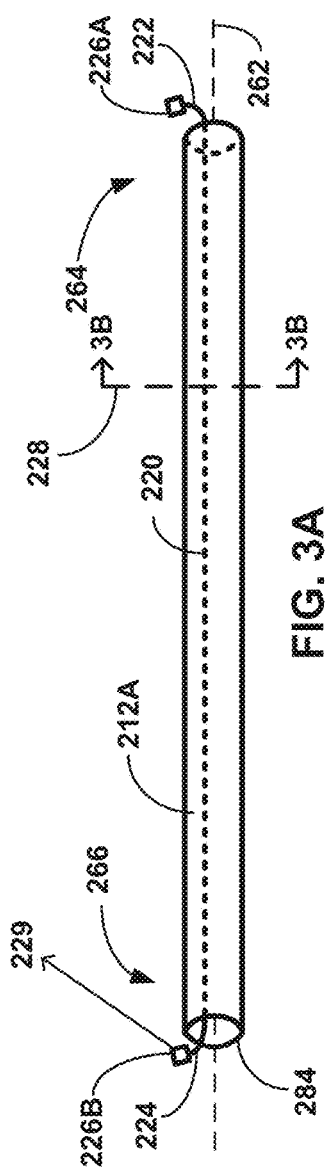
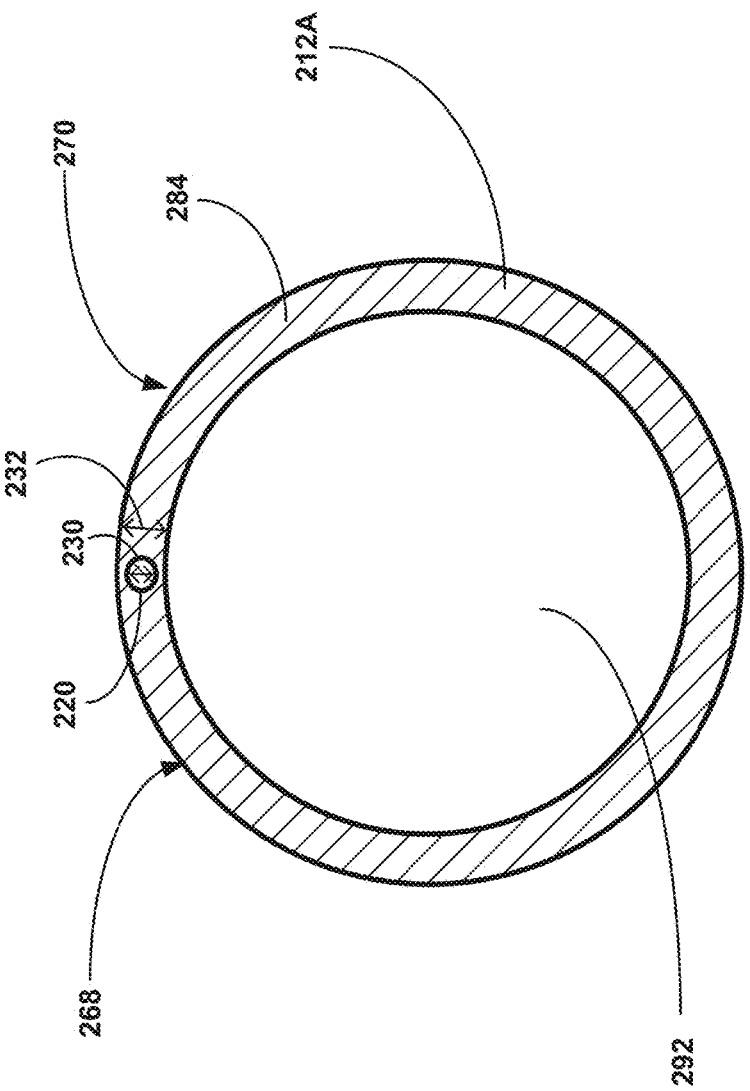

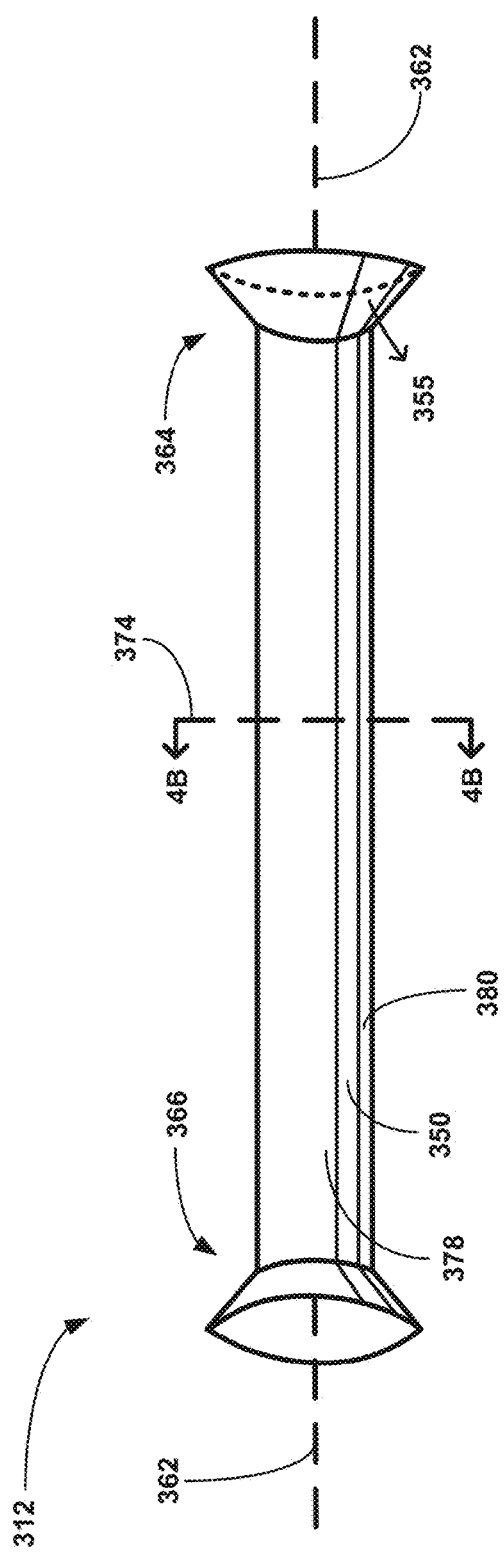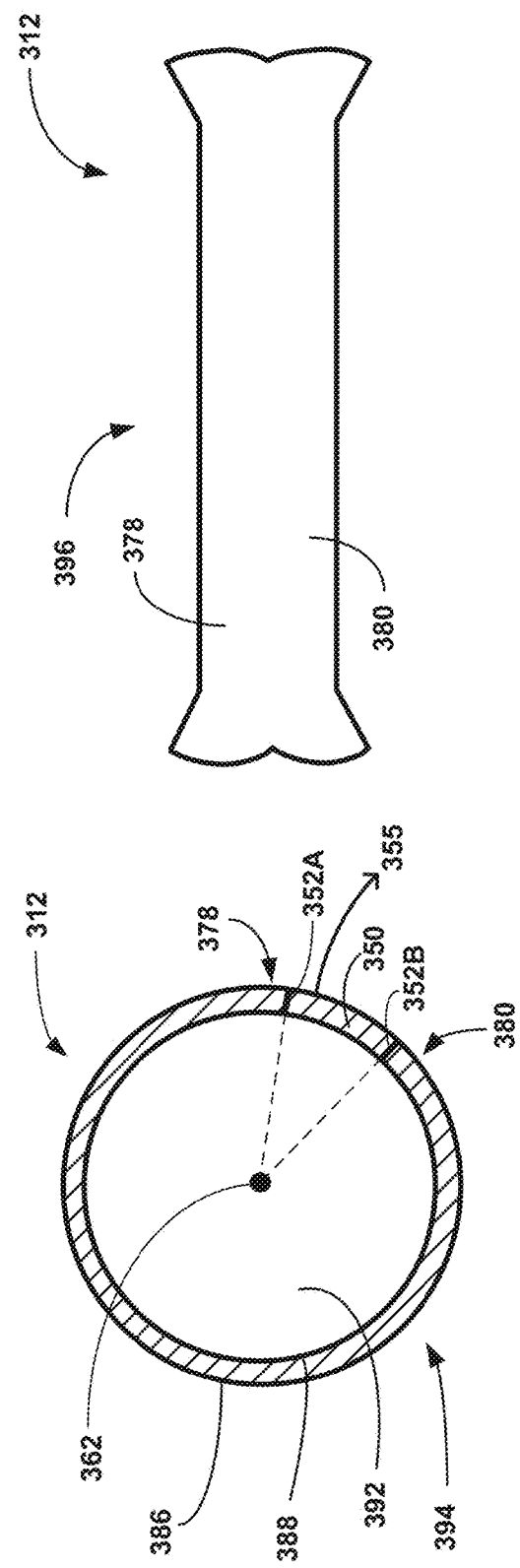
FIG. 5A
FIG. 5B
FIG. 5C

EXPANDABLE BALLOON SHEATHS

RELATED APPLICATIONS

This application is a continuation of application Ser. No. 15/875,343, entitled "EXPANDABLE BALLOON SHEATHS," filed Jan. 19, 2018, the contents of which are incorporated by reference in their entirety.

TECHNICAL FIELD

This disclosure relates to medical sheaths, and more specifically expandable balloon sheaths.

BACKGROUND

Some medical treatments include the use of inflatable balloons. The expandable balloon may be inserted in a patient, such as within the vasculature of a patient, and navigated to a target site to be treated within the patient. Some expandable balloons may be fragile, such that it is easy for expandable balloons to incur damage during the insertion process. Further, some expandable balloons include coatings, such as drug coatings, which may be damaged or lost during insertion and/or navigation to the target site.

SUMMARY

In some aspects, this disclosure describes a medical device including a tubular sheath for enclosing an expandable balloon. The tubular sheath may be used with a catheter having an expandable balloon attached to the distal portion of the catheter, such that the tubular sheath encloses and protects the expandable balloon. The tubular sheath may enclose the expandable balloon during at least shipment and pre-insertion handling of the expandable balloon. The tubular sheath may be configured to enclose the expandable balloon up to and substantially through the process of inserting the expandable balloon into the body of a patient through an introducer sheath. The tubular sheath may be configured to be slideable and removeable from the catheter. The tubular sheath may include a longitudinal splitting element and may be configured to be removeable as a result of a force applied to the longitudinal splitting element. The longitudinal splitting element may be configured to split the wall of the tubular sheath in response to the force. Alternatively, the tubular sheath may include a gripping portion that has relatively poor cohesive strength to adjacent portions of the tubular sheath. The tubular sheath may be configured to be removable in response to a force applied to the gripping portion.

In a first example, aspects of the disclosure relate to a medical device that includes a catheter configured to navigate vasculature of a patient after insertion through an introducer sheath inserted in the patient, the catheter comprising a distal portion and a proximal portion. The medical device also includes an expandable balloon that is attached to the distal portion of the catheter and a tubular sheath configured to enclose the expandable balloon. The tubular sheath includes at least one longitudinal splitting element within a wall of the tubular sheath, the at least one longitudinal splitting element being configured to split the wall of the tubular sheath in response to a force greater than a threshold force upon the at least one longitudinal splitting element. The at least one longitudinal splitting element extends from a proximal end of the tubular sheath to a distal end of the tubular sheath.

In a second example relating to the medical device of the first example, the at least one longitudinal splitting element includes a wire embedded longitudinally along a length of the tubular sheath, the wire configured to extend out from at least one of the proximal end and distal end of the tubular sheath, wherein the wire is configured to split the tubular sheath as a result of pulling the wire out from the wall.

In a third example relating to the medical device of the second example, the medical device includes a tab that is attached to an end of the wire that extends out from the at least one end of the tubular sheath.

In a fourth example relating to the medical device of the first example, the at least one longitudinal splitting element includes two or more sets of holes that extend longitudinally through a wall of the tubular sheath from the proximal end of the tubular sheath to the distal end of the tubular sheath, wherein the two or more sets of holes are configured to split the tubular sheath as a result of stressing the tubular sheath along the two or more sets of holes.

In a fifth example relating to the medical device of the fourth example, each set of holes includes two or more holes that are arranged radially from an inner surface of the tubular sheath to an outer surface of the inner sheath.

In a sixth example relating to the medical device of the fourth and fifth examples, the tubular sheath includes one or more grooves that extend radially in from an outer surface of the tubular sheath and extend longitudinally from the proximal end of the tubular sheath to the distal end of the tubular sheath, wherein each groove is radially in-line with one of the two or more sets of holes.

In a seventh example relating to the medical device of any of the fourth through sixth examples, sets of holes are arranged 180° apart across the longitudinal axis of the tubular sheath.

In an eighth example relating to the medical device of any of the first through seventh examples, the tubular sheath includes at least one of poly(tetrafluoroethylene), high density polyethylene, or low density polyethylene.

In a ninth example relating to the medical device of any of the first through eighth examples, a thickness of the wall of the tubular sheath is substantially constant throughout the tubular sheath.

In a tenth example relating to the medical device of any of the first through ninth examples, the medical device further includes a Luer fitting at a distal end of the tubular sheath, wherein the Luer fitting includes a structural weakness aligned with the at least one longitudinal splitting element to enable the Luer fitting to be controllably split along the structural weakness.

In an eleventh example relating to the medical device of any of the first through tenth examples, the tubular sheath is configured to be received by the introducer sheath during insertion of the catheter into the introducer sheath such that the tubular sheath remains stationary relative to the introducer sheath while sliding proximally relative to the catheter as the catheter is inserted distally at least until the expandable balloon is fully inserted into the introducer sheath without substantial contact between the tubular sheath and the expandable balloon.

In a twelfth example, aspects of the disclosure relate to a medical device that includes a catheter configured to navigate vasculature of a patient after insertion into an introducer sheath inserted in the patient where the catheter includes a distal portion and a proximal portion, an expandable balloon that is attached to the distal portion of the catheter and a tubular sheath that includes a gripping portion. The tubular sheath is configured to enclose the expandable balloon and the gripping portion of the tubular sheath has relatively poor cohesive strength to adjacent portions of the tubular sheath such that the tubular sheath is configured to be split along the gripping portion to enable the tubular sheath to be splittably removeable from the catheter. The gripping portion of the tubular sheath extends from a proximal end of the tubular sheath to a distal end of the tubular sheath and the gripping portion of the tubular sheath extends through a thickness of a wall of the tubular sheath.

In a thirteenth example relating to the medical device of the twelfth example, an external surface of the expandable balloon includes a drug coating.

In a fourteenth example relating to the medical device of the twelfth and thirteenth examples, the expandable balloon is in a deflated state on the distal portion of the catheter and a diameter of the inner lumen of the tubular sheath is configured to be greater than an outer diameter of the expandable balloon in the deflated state.

In a fifteenth example relating to the medical device of the fourteenth example, a length of the tubular sheath along the longitudinal axis of the tubular sheath is greater than a length of the expandable balloon along a longitudinal axis of the expandable balloon in the deflated state.

In a sixteenth example relating to the medical device of any of the twelfth through fifteenth examples, the expandable balloon is a percutaneous transluminal angioplasty (PTA) balloon.

In a seventeenth example relating to the medical device of any of the twelfth through sixteenth examples, the gripping portion of the tubular sheath includes a first material and adjacent portions of the tubular sheath include a second material, where the first and second material are configured to have a relatively poor bond to each other and the tubular sheath is configured to be splittable as a result of pulling the gripping portion away from the adjacent portions.

In an eighteenth example relating to the medical device of the seventeenth example, the medical device includes a tab that is attached to the gripping portion of the tubular sheath at an end of the gripping portion to facilitate pulling of the gripping portion.

In a nineteenth example relating to the medical device of the seventeenth and eighteenth examples, the first material is a different color than the second material.

In a twentieth example relating to the medical device of any of the twelfth through sixteenth examples, the gripping portion of the tubular sheath includes a first material and adjacent portions of the tubular sheath include a second material, where the first material has a greater tensile strength than the second material.

In a twenty-first example relating to the medical device of the twentieth example, the medical device includes a tab that is attached to the gripping portion of the tubular sheath at an end of the gripping portion to facilitate pulling of the gripping portion.

In a twenty-second example relating to the medical device of any of the twelfth through sixteenth examples, the gripping portion and the adjacent portions converge at two parallel lines of perforations that extend longitudinally from the proximal end of the tubular sheath to the distal end of the tubular sheath and each line of perforation cuts through the wall of the tubular sheath. The medical device includes a tab that is attached to the proximal or distal end of the gripping portion and the tubular sheath is configured to be splittable as a result of pulling the tab and disengaging the first material from the second material.

In a twenty-third example relating to the medical device of any of the twelfth through twenty-second examples, the tubular sheath is configured to be received by the introducer sheath during insertion of the catheter into the introducer sheath such that the tubular sheath remains substantially stationary relative to the introducer sheath while sliding proximally relative to the catheter as the catheter is inserted distally at least until the expandable balloon is fully inserted into the introducer sheath without substantial contact between the tubular sheath and the expandable balloon.

In a twenty-fourth example, aspects of the disclosure relate to a method of inserting expandable balloons that includes locating a distal portion of a catheter of a medical device immediately proximal to an introducer sheath inserted in a patient. The medical device includes an expandable balloon that is attached to the distal portion of the catheter and a tubular sheath configured to enclose the expandable balloon, wherein a gripping portion of the tubular sheath has relatively poor cohesive strength to adjacent portions of the tubular sheath such that the tubular sheath is configured to be split along the gripping portion to enable the tubular sheath to be splittably removeable from the catheter. The gripping portion of the tubular sheath extends from a proximal end of the tubular sheath to a distal end of the tubular sheath and extends through a thickness of a wall of the tubular sheath. The method of inserting expandable balloons also includes distally pushing the catheter into the introducer sheath such that the tubular sheath remains stationary relative to the introducer sheath while sliding proximally relative to the catheter as the catheter is inserted distally at least until the expandable balloon is fully inserted into the introducer sheath without substantial contact between the tubular sheath and the expandable balloon. The method of inserting expandable balloons also includes splitting the tubular sheath using the gripping portion to remove the tubular sheath from the catheter in response to fully inserting the expandable balloon into the introducer sheath.

In a twenty-fifth example, aspects of the disclosure relate to a method of inserting expandable balloons that includes locating a distal portion of a catheter of a medical device immediately proximal to an introducer inserted in a patient. The medical device includes an expandable balloon that is attached to the distal portion of the catheter and a tubular sheath configured to enclose the expandable balloon, where the tubular sheath includes at least one longitudinal splitting element within a wall of the tubular sheath. The at least one longitudinal splitting element is configured to split the wall of the tubular sheath in response to a force greater than a threshold force upon the at least one longitudinal splitting element and also extends from a proximal end of the tubular sheath to a distal end of the tubular sheath. The method of inserting expandable balloons also includes distally pushing the catheter into the introducer sheath such that the tubular sheath remains stationary relative to the introducer sheath while the tubular sheath slides proximally relative to the catheter as the catheter is inserted distally at least until the expandable balloon is fully inserted into the introducer sheath without substantial contact between the tubular sheath and the expandable balloon. The method of inserting expandable balloons also includes splitting the tubular sheath using the at least one longitudinal splitting element to remove the tubular sheath from the catheter in response to fully inserting the expandable balloon into the introducer sheath.

The details of one or more examples are set forth in the accompanying drawings and the description below. Other features, objects, and advantages will be apparent from the description and drawings, and from the claims.

BRIEF DESCRIPTION OF THE DRAWINGS

FIG. 1A is a conceptual and schematic diagram illustrating a view of an example medical device including an example tubular sheath enclosing an example expandable balloon on an example catheter near an example introducer sheath inserted in a body of a patient.

FIGS. 1B-1D are conceptual and schematic views of the medical device of FIG. 1A, including a cross-sectional view of the catheter of FIG. 1A (FIG. 1B), a view of the expandable balloon on the catheter without the tubular sheath of FIG. 1A (FIG. 1C), and the tubular sheath of FIG. 1A (FIG. 1D).

FIGS. 2A-2D are conceptual and schematic diagrams illustrating a side view of an example tubular sheath with a longitudinal splitting element (FIG. 2A), a side view of an example tubular sheath with a spirally configured splitting element (FIG. 2B), a cross-sectional view taken along cross-sectional cut plane 174 in FIG. 2A (FIG. 2C), and a side view of an example tubular sheath in a split configuration (FIG. 2D).

FIGS. 3A and 3B are conceptual and schematic diagrams illustrating a side view of a tubular sheath with a first example longitudinal splitting element (FIG. 3A) and a cross-sectional view of the tubular sheath of FIG. 3A taken along cross-sectional cut plane 228 (FIG. 3B).

FIGS. 5A-5C are conceptual and schematic diagrams illustrating a side view of another example tubular sheath with a first example gripping portion in the enclosing configuration (FIG. 5A), a cross-sectional view of the tubular sheath of FIG. 5A taken along cross-sectional cut plane 374 (FIG. 5B), and a side view of the tubular sheath of FIG. 5A in a split configuration (FIG. 5C).

DETAILED DESCRIPTION

Figure 4A:
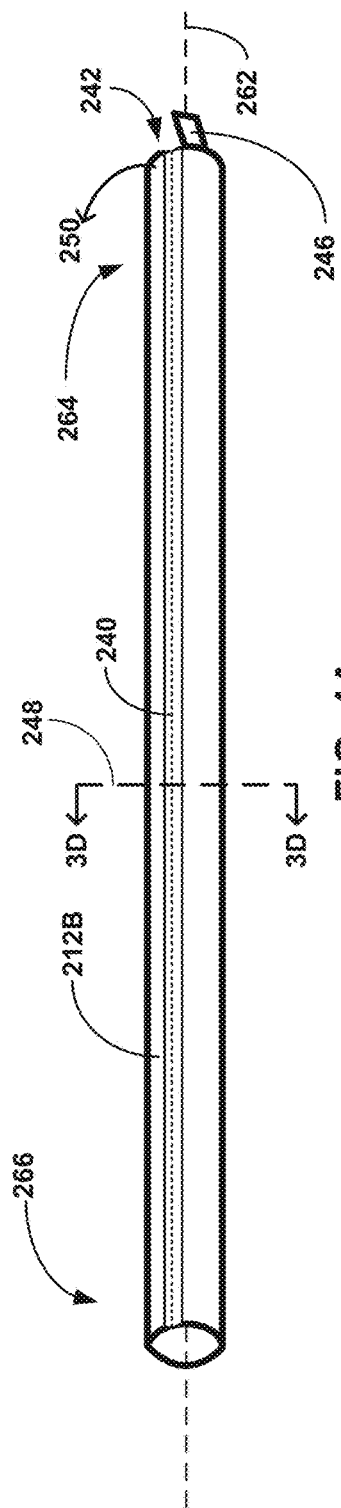
FIGS. 4A and 4B are conceptual and schematic diagrams illustrating a side view of a tubular sheath with a second example longitudinal splitting element (FIG. 4A), and a cross-sectional view of the tubular sheath of FIG. 4A taken along the cross-sectional cut plane 248 (FIG. 4B).

In general, the disclosure describes an example medical device that includes a tubular sheath that encloses an expandable balloon on the distal portion of a catheter. The medical device may be used, in part, to enclose an expandable balloon during packaging, storing, and inserting of the expandable balloon into a body of a patient. The tubular sheath is configured to split open. The tubular sheath may include a longitudinal splitting element, a gripping portion to facilitate splitting the tubular sheath, or both.

Expandable medical balloons are used in a variety of medical procedures, such as angioplasty, tuboplasty, or pyeloplasty. In medical procedures, the expandable balloon may be attached to a catheter that is configured to be manipulated to navigate the expandable balloon to a target site. The target site may be a location within a patient's body where an ailment of the patient's body is treated. In some medical procedures, the expandable balloon may be navigated to the target site in an unexpanded (deflated) state and then expanded (inflated) at the target site as part of the medical procedure.

The expandable balloon may be relatively delicate, being prone to kinking or flexing in ways that damage the structural integrity of the expandable balloon. For example, if handled improperly, the expandable balloon may become stuck to itself or become stretched, such that upon being inflated, the expandable balloon may not inflate evenly or in the intended shape, or may inflate with an undesired weakness (e.g., the weakness making the expandable balloon more susceptible to popping/breaking). Additionally, the catheter to which the expandable balloon is attached may be relatively delicate, such that prolonged or forceful manipulation may result in a portion of the catheter buckling or breaking. For example, in response to a clinician having difficulty inserting an expandable balloon into a patient (e.g., where a clinician has a difficult angle of entry or is having difficulty fitting the expandable balloon into an introducer sheath as described herein), the catheter may be prone to buckling or breaking at a location proximal to the point of insertion. In some examples, the expandable balloon may be damaged as described above in response to the catheter buckling or breaking, such that it is difficult or impossible to utilize the damaged expandable balloon. In other examples, the catheter itself may be difficult or impossible to use upon buckling or breaking, such that it may be difficult or impossible to insert and therein utilize the expandable balloon while the expandable balloon is attached to the damaged catheter.

The tubular sheaths described herein may enclose and protect or shield the expandable balloon until it is no longer possible/practicable to enclose the expandable balloon (e.g., upon inserting the expandable balloon into an introducer sheath inserted in a patient). By enclosing the expandable balloon substantially through insertion, the tubular sheath may facilitate insertion of the expandable balloon, thus reducing the likelihood of buckling or otherwise damaging the catheter as a result of a difficult insertion. Further, enclosing the expandable balloon in a tubular sheath described herein may reduce or substantially eliminate contact between the expandable balloon and a user such as a clinician that is manipulating the expandable balloon or catheter. Providing this tubular support for the expandable balloon and catheter during operation (e.g., insertion into the patient's anatomy such as peripheral arteries) may reduce the likelihood of kinking or flexing the expandable balloon. Additionally, the tubular sheath may be configured to slide along the catheter, such that during insertion the tubular sheath may stay proximal to an introducer sheath while the expandable balloon and catheter slide distally through tubular sheath. By configuring the tubular sheath to slide along the catheter, the tubular sheath may provide support to the most vulnerable portion of the catheter (e.g., the portion of the catheter immediately proximal to the point of insertion), thus reducing the likelihood of the catheter buckling or otherwise becoming damaged during insertion.

Further, in some expandable balloons, an external surface of the expandable balloon may be coated with a drug, which is delivered to the target site upon expanding the expandable balloon. For example, the drug may be intended to stop a hyperproliferative response of an intima within the vasculature of a patient. Such drug coatings may have relatively low adhesion to the expandable balloon such that contact between the drug coating and other surfaces or structures may remove some drug coating from the external surface of the expandable balloon. This may increase variability and/or unpredictability in an amount of drug delivered to the target site, both of which are undesirable. The tubular sheaths described herein may reduce inadvertent removal of drug from the surface of a coated expandable balloon (e.g., due to contact with a user such as a clinician that is manipulating the balloon or catheter). One advantage of the tubular sheaths described here is that they can each be removed relatively easily without damaging the expandable balloon or any coating while providing tubular support for both the expandable balloon and the catheter during insertion into the patient's anatomy (e.g., peripheral arteries). Further, the tubular sheath may reduce the likelihood of drug transfer to a clinician handling the expandable balloon by enclosing the drug coating substantially through insertion of the expandable balloon into a patient.

In some examples, tubular sheaths described herein may include one or relatively few components rather than multiple components. Configuring a tubular sheath such that the tubular sheath is made from one or relatively few components may reduce the difficulty of manufacturing, assembling, and/or using the tubular sheaths. In some examples, the appearance and dimensions of the tubular sheaths described herein may be substantially similar or identical to other non-splittable and/or non-slidable sheaths, which may enable a clinician to recognize and more quickly understand the nature and operability of the tubular sheaths. Additionally, by configuring the tubular sheaths described herein to be like other non-splittable and/or non-slidable sheaths, the tubular sheaths described herein may be relatively easier to integrate into existing manufacturing processes or treatment procedures (e.g., tubular sheaths may be configured to utilize existing packaging and define dimensional fits with expandable balloons according to existing manufacturing procedures).

FIG. 1A is a conceptual and schematic diagram illustrating a view of an example medical device 10 including an example tubular sheath 12 that is enclosing an expandable balloon 14 that is attached to a catheter 16. The expandable balloon 14 may be attached to the catheter 16 adjacent to a distal portion 18 of the catheter 16. In some examples, the expandable balloon 14 is fixedly attached adjacent to the distal portion 18 of the catheter 16, such that it is difficult or impossible to remove the expandable balloon 14 from the catheter 16 without damaging one or both of the expandable balloon 14 or the catheter 16. In other examples, the expandable balloon 14 is loosely or removably attached to the catheter 16, such that the expandable balloon 14 may be detached from the catheter 16 once the expandable balloon 14 is navigated to the target site.

In some examples, the system in which the medical device 10 is utilized may include an introducer sheath 22. The introducer sheath 22 may be inserted into the patient transcutaneously in order to access a vasculature 24 of a patient 26. In some examples, the introducer sheath 22 may include external threads 23, which may be configured to mate with complementary threads defined in the tubular sheath 12. In other examples, the introducer sheath 22 may omit the external threads 23. An internal diameter of the introducer sheath 22 may be selected to accommodate an external diameter of the expandable balloon 14 (e.g., in a deflated state) and an external diameter of the catheter 16. Alternatively, some or all of the internal diameter of the introducer sheath 22 may be selected to accommodate an external diameter of the tubular sheath 12 in examples where the tubular sheath 12 is configured to be inserted into the introducer sheath 22. For example, a proximal-most internal diameter of the introducer sheath 22 may be selected to accommodate external diameters of the catheter 16, the expandable balloon 14, and the tubular sheath 12, while a relatively distal internal diameter of the introducer sheath 22 is selected to accommodate an external diameter of the catheter 16 and the expandable balloon 14 and not the tubular sheath 12. In such an example, the tubular sheath 12 may be inserted past the initial external diameter of the introducer sheath 22 and then be received (e.g., stopped) by the secondary internal diameter of the introducer sheath 22, while the expandable balloon 14 and catheter 16 are dimensioned to distally move through the entirety of the introducer sheath 22.

The vasculature 24 of the patient 26 into which the introducer sheath 22 is inserted may be selected to provide access to a selected target site to which the expandable balloon 14 will be advanced. For example, the expandable balloon 14 may be used to provide anti-restenotic therapy to a target site in peripheral vasculature of a patient 26.

The catheter 16 extends from a proximal portion 36 adjacent to a hub 38, such as a manifold, to the distal portion 18. The expandable balloon 14 is connected to the distal portion 18 of the catheter 16. The catheter 16 may include structural features that enable expansion or inflation of the expandable balloon 14 and advancing of the expandable balloon 14 to the target site in the patient 26. For example, the catheter 16 may include a guidewire lumen 42 and an inflation lumen 44, as shown in FIG. 1B.

FIG. 1B is a cross-sectional view of the catheter 16 taken along the cross-sectional cut plane 40 in FIG. 1A. The guidewire lumen 42 may be configured to receive a guidewire 20. In some examples, the guidewire lumen 42 may extend longitudinally through the catheter 16 from the distal portion 18 to the hub 38. The hub 38 may include a first port that provides access to the guidewire lumen 42 to facilitate advancing the catheter 16 along the guidewire 20. Similarly, the inflation lumen 44 may extend longitudinally through the catheter 16 from the hub 38 to the expandable balloon 14. The hub 38 may include a second port that provides access to the inflation lumen 44. The inflation lumen 44 may terminate distally at an orifice to the interior of the expandable balloon 14. The inflation lumen 44 may be configured to receive a fluid that is flowed into the inflation lumen 44 from the hub 38 to expand or inflate the expandable balloon 14 (e.g., once the expandable balloon 14 has been navigated to the target site).

FIG. 1C is a conceptual and schematic diagram illustrating a side view of the expandable balloon 14 as arranged on the catheter 16 without the tubular sheath 12. As depicted in FIG. 1C, the expandable balloon 14 is in a deflated configuration 46, which includes the expandable balloon 14 being folded or "pleated" into a physically smaller profile than the profile of the expandable balloon 14 in an inflated configuration. It is to be understood that the general shape of the deflated configuration 46 in FIG. 1C is for illustration purposes only; other shapes and configurations of the expandable balloon 14 in a non-inflated (e.g., deflated) configuration 46 are also possible. Further, as depicted in FIG. 1C, the guidewire 20 extends from a position distal to the expandable balloon 14 longitudinally through the catheter 16 to the hub 38. In some examples, the guidewire 20 may be advanced through the vasculature 24 of a patient 26 during a previous step, such that the catheter 16 is advanced over the guidewire 20 using the guidewire lumen 42 to navigate the expandable balloon 14 to the target site (e.g., using the Seldinger technique). During such a technique, the guidewire 20 may only extend as far proximally through the guidewire lumen 42 as the catheter 16 has been pushed distally along the guidewire 20.

The expandable balloon 14 may be formed from any suitable material that provides sufficient strength and flexibility for the pressures experienced by the expandable balloon 14 during the inflation procedure. The materials from which the expandable balloon 14 is formed may be biocompatible and compatible with a drug coating on the external surface 48 of the expandable balloon 14. In some examples, materials from which the expandable balloon 14 is formed may include nylon, polyethylene terephthalate (PET), polyethylene (such as crosslinked polyethylene), polyurethane, polyvinyl chloride, silicone elastomer, or the like.

In some examples, the expandable balloon 14 may include a coating on an external surface 48 of the expandable balloon. The coating may include, for example, a lubricious coating (either hydrophilic or hydrophobic), a drug coating, or the like. In some examples, the drug coating may include a drug selected to treat peripheral artery disease, such as an anti-restenotic or anti-proliferative drug. An example anti-proliferative drug is paclitaxel. In some examples, the drug coating may further include an excipient to facilitate release of the drug from the drug coating. Example excipients include urea, polysorbate, sorbitol, or the like.

FIG. 1D is a conceptual and schematic diagram illustrating a side view of the tubular sheath 12. The tubular sheath 12 may be made of any of a number of suitable materials, such as poly(tetrafluoroethylene) (PTFE), high density polyethylene (HDPE), or low density polyethylene (LDPE). The tubular sheath 12 is configured to enclose the expandable balloon 14 until the expandable balloon is inserted into the vasculature 24 of a patient 26 and/or inserted into an introducer sheath 22 inserted within the vasculature 24 of a patient 26. Configuring the tubular sheath 12 to enclose the expandable balloon 14 through the process of insertion may reduce the necessity or possibility of manual handling of the expandable balloon 14. Reducing the possibility or necessity of manual handling of the expandable balloon 14 may result in structural or pharmaceutical benefits for the medical device 10, as manually handling the expandable balloon 14 may physically damage the expandable balloon 14, the shaft of the catheter 16, or both, unnecessarily remove any drug coating from the expandable balloon 14, or both.

As discussed herein, the tubular sheath 12 is configured to be slideable along the catheter and splittably removeable from the catheter 16. The tubular sheath 12 may be removed in conjunction with the expandable balloon 14 being inserted into the body of a patient 26. In some examples, the tubular sheath 12 may be removed from the catheter 16 as a result of a sufficient force being applied to a gripping portion that has relatively poor cohesive strength to adjacent portions of the tubular sheath 12. In other examples, the tubular sheath 12 may be removed from the catheter 16 as a result of a sufficient force being applied to one or more longitudinal splitting elements within a wall of the tubular sheath that are configured to split the tubular sheath 12. The force may be applied by a user, such as a clinician. A sufficient force may be a force above a threshold amount of force. The threshold amount of force should be selected to be sufficiently low to enable a user such as a clinician to split the tubular sheath 12 and sufficiently high to reduce inadvertent splitting of the tubular sheath, for example, due to inadvertent catching of the tubular sheath on another structure during manufacturing, storage, shipping, or handling prior to the treatment procedure.

The tubular sheath 12 is configured to enclose the expandable balloon 14. For example, the tubular sheath 12 may be configured to enclose the expandable balloon 14 during storage, handling, and at least an initial portion of a treatment procedure. The tubular sheath 12 may be configured to support the expandable balloon 14, catheter 16, or both during the insertion of the expandable balloon 14 (e.g., insertion into the introducer sheath 22) to reduce or substantially eliminate bending and kinking of the expandable balloon 14, catheter 16, or both during insertion into the introducer sheath 22. In some examples, the tubular sheath 12 may be sized relative to the expandable balloon 14 so that contact between the expandable balloon 14 and the tubular sheath 12 is reduced or minimized. For example, an internal diameter 28 of the tubular sheath 12 may be greater than an external diameter 30 of the expandable balloon 14 when the expandable balloon 14 is in the deflated configuration 46. Further, a longitudinal length 32 of the tubular sheath 12 may be greater than a longitudinal length 34 of the expandable balloon 14. For example, the tubular sheath 12 may be at least 300 millimeters long (e.g., as such a length may cover many varieties of expandable balloons 14). Configuring the tubular sheath 12 to substantially cover the expandable balloon 14 while reducing or minimizing contact between the tubular sheath 12 and the expandable balloon 14 may increase the physical integrity of both the expandable balloon 14 and any drug coating on the expandable balloon 14, as contact may result in either or both a portion of the drug coating being partially removed and one or more of the expandable balloon 14 and/or catheter 16 kinking.

The tubular sheath 12 may be configured to define a relatively reduced profile, such that an outer diameter 35 of the tubular sheath 12 is nearly equal to an external diameter 30 of the deflated state of the expandable balloon 14 (e.g., the tubular sheath 12 may define an external diameter 30 that is less than two times the external diameter 30 of the deflated state of the expandable balloon 14). In some examples, the outer surface of the tubular sheath 12 may define a generally continuous and tubular outer surface (e.g., an outer surface that does not define large ridges or lips that double or triple a diameter of the tubular sheath 12). Put differently, a longitudinal profile of the tubular sheath 12 may be configured to avoid extending out radially from the relative shape of the expandable balloon 14 more than what facilitates moving the tubular sheath 12 on the catheter 16 as described herein. For example, other than a proximal flare 50 and distal flare 52 as discussed below with respect to FIG. 1D, tubular sheath 12 may omit features that substantially extend radially outward (e.g., extend outward to more than two or three times an internal diameter 28 of the tubular sheath 12).

The expandable balloon 14 may be stored and shipped attached to the catheter 16 within a channel or lumen of a container, where removing the expandable balloon 14 and catheter 16 from the container may include a clinician longitudinally extracting the catheter 16 (and the expandable balloon 14) through the channel or lumen. In examples in which a clinician removes the medical device 10 from a container by longitudinally traversing the medical device 10 through a channel or lumen, the channel or lumen of a container must be at least as large as the greatest radius as the medical device 10 that the container will store. Thus, reducing the longitudinal profile of the tubular sheath 12 may reduce a size of the container used to store the medical device 10.

The tubular sheath 12 may be configured to generally maintain a stable position on the catheter 16 relative to the catheter 16 as the catheter 16 is handled. For example, the tubular sheath 12 may be configured to maintain a position over the expandable balloon 14 such that the tubular sheath 12 substantially always houses the expandable balloon 14 as the catheter 16 is handled/moved by a clinician (e.g., whether or not the clinician is specifically handling/holding the tubular sheath 12 in place) until insertion of the expandable balloon 14 into the introducer sheath 22. In some examples, the tubular sheath 12 is configured to be moved relative to the catheter 16 (e.g., subsequent to a retaining member exposing the expandable balloon 14 as described herein) in response to the clinician applying more than a threshold force upon the tubular sheath 12 and/or a retaining member as described herein, where the threshold force is more than a nominal force (e.g., gravity or incidental contact as a result of the tubular sheath 12 unintentionally or otherwise minimally contacts an object). The tubular sheath 12 may be configured to maintain a relatively stable position on the catheter 16 because of a fit of the tubular sheath 12 on the expandable balloon 14 (e.g., a friction fit). Configuring the tubular sheath 12 to generally maintain a stable position on the catheter 16 relative to the catheter 16 while a clinician is handling the medical device 10, whether or not the tubular sheath 12 is purposefully externally supported (e.g., supported by the clinician) during such handling, may improve an ability of the tubular sheath 12 to house and protect the expandable balloon 14, catheter 16, or both during handling and insertion of the expandable balloon 14 and the catheter 16 into introducer sheath 22.

In some examples, the tubular sheath 12 is configured to slide proximally relative to the catheter 16 as the catheter 16 is pushed distally into the introducer sheath 22. In certain examples, the tubular sheath 12 may be further configured to structurally support the expandable balloon 14, catheter 16, or both during insertion (e.g., to help one or both of the expandable balloon 14 or catheter 16 avoid kinking or bending). For example, the tubular sheath 12 may create a Luer connection with the introducer sheath 22 (e.g., using external threads 23 on the introducer sheath 22) to provide additional support to one or both of the expandable balloon 14 or catheter 16 during insertion. By being configured to slide proximally relative to the catheter 16 while supporting the expandable balloon 14, catheter 16, or both as a clinician feeds the catheter 16 into the introducer sheath 22, the tubular sheath 12 protects the expandable balloon 14 until the expandable balloon 14 is substantially fully inserted into the introducer sheath 22. This may reduce or substantially eliminate manual handling of the expandable balloon 14 by a user such as a clinician, which may result in structural or pharmaceutical benefits for the medical device 10. For example, manually handling the expandable balloon 14 may increase the risk of physically damaging one or both of the expandable balloon 14 or catheter 16 or unnecessarily removing drug coating from the expandable balloon 14, such that avoiding manually handling the expandable balloon 14 is advantageous.

Further, configuring the tubular sheath 12 to be both removable and slideable on the catheter 16 may increase the operational length of the catheter 16 during a medical procedure. For example, if a tubular sheath 12 was slideable but not removable, in response to the tubular sheath 12 being slid proximally back to a proximal portion 36 of the catheter, a length of the catheter 16 that is equal or greater to the length 32 of the tubular sheath 12 may be operationally unusable (e.g., as the tubular sheath 12 may be neither able to slide proximally over the hub 38 of the catheter 16 nor able to be inserted into the introducer sheath 22). In some examples, it may be advantageous to delay removing the tubular sheath 12 from the catheter 16 until the expandable balloon 14 is distally past the introducer sheath 22 into the vasculature 24 of the patient 26, as the act of insertion may be complicated and prone for error (such that minimizing the steps thereof is useful in reducing the likelihood of error) in comparison to the act of vasculature 24 navigation.

As depicted in FIG. 1D, in some examples, the tubular sheath 12 may be configured with a proximal flare 50 and distal flare 52, such that a proximal end 64 and distal end 66 of the tubular sheath 12 may flare outward from a middle section of the tubular sheath 12. The proximal flare 50 may be configured to facilitate proximal sliding of the tubular sheath 12 over a catheter 16. The distal flare 52 may be configured to facilitate distal sliding of the tubular sheath 12 over the expandable balloon 14, forming a contact fit with the insertion sheath 22, or the like. In other examples (not depicted), the distal flare 52 may flare to a different final diameter or may flare at a different angle relative to the proximal flare 50. In certain examples, the tubular sheath 12 may have a proximal flare 50 but not a distal flare 52, or vice versa, or no flare at all.

As discussed herein, the tubular sheath 12 is configured to split in response to application of a force above a threshold force to a structural feature of the tubular sheath 12, such as a longitudinal splitting element or a gripping element. Several different example mechanisms for splitting the tubular sheath 12 are discussed within this disclosure. For example, the tubular sheath may include a plurality of longitudinal perforations or a longitudinal slit or cut, any of which may be configured to make the tubular sheath 12 splittable. Each slit, cut, or perforation may cut substantially through one side of the tubular sheath 12. The slit, cut, or plurality of perforations may extend from a proximal end 64 of the tubular sheath 12 to a distal end 66 of the tubular sheath 12. While in some examples the slit, cut, or perforations may be substantially parallel with a longitudinal axis 62 of the tubular sheath 12, in other examples the slit, cut, or perforations may be at an angle relative to the longitudinal axis 62 of the tubular sheath 12 or may spiral around the longitudinal axis 62 of the tubular sheath 12. Further, while in some examples the tubular sheath 12 may include a single slit, cut, or line of perforations, in other examples, the tubular sheath 12 may include two or more slits, cuts, or lines of perforations extending along the tubular sheath 12. Other mechanisms for splitting tubular sheaths 12 may include a wire embedded in a wall of a tubular sheath 12, longitudinal holes within a wall of a tubular sheath 12, longitudinal grooves along a wall of a tubular sheath 12, a pair of longitudinal perforations defining a gripping portion of a tubular sheath 12, or a longitudinal subsection of the tubular sheath 12 that has relatively poor cohesive strength to adjacent portions of the tubular sheath 12 to define a gripping section, each of which are described in further detail below.

FIGS. 2A-2D are conceptual and schematic diagrams illustrating an example tubular sheath 112 having a longitudinal splitting element 160 in various configurations. The tubular sheath 112 may be substantially similar to the tubular sheath 12 of FIG. 1A, aside from the differences described herein. As depicted in FIG. 2A, the tubular sheath 112 may have a relatively consistent profile between a proximal end 164 and distal end 166 of the tubular sheath 112. For example, the tubular sheath 112 may have a relatively consistent radius 172 throughout the tubular sheath 112. In other examples, the tubular sheath 112 may define a number of distinct profiles or have a varying profile between the proximal end 164 and distal end 166 of the tubular sheath 112, so long as the tubular sheath 112 is configured to substantially enclose the expandable balloon 14 while reducing contact with the expandable balloon 14.

The tubular sheath 112 may include a longitudinal splitting element 160. The longitudinal splitting element 160 may be a feature of the tubular sheath 112 that is within a wall of the tubular sheath 112 and is configured to split the tubular sheath 112. The longitudinal splitting element 160 may extend along a longitudinal axis 162 of the tubular sheath 112. The splitting element 160 may extend from a proximal end 164 of the tubular sheath 112 to a distal end 166 of the tubular sheath 112. The splitting element 160 may define two sides 168, 170 of the tubular sheath 112 on either side of the splitting element 160. The splitting element 160 may be configured to split the tubular sheath 112 between the two sides 168, 170 in response to a force above a threshold force being applied to the splitting element 160 or to the two sides 168 and 170 in opposite directions. The longitudinal splitting element 160 may include, for example, a wire embedded in a wall 184 (FIG. 2C) of the tubular sheath 112, a plurality of longitudinal perforations formed in the wall 184 of the tubular sheath 112, a combination of a wire embedded in the wall 184 with perforations formed in the wall 184 adjacent to the wire, or the like.

In some examples, the splitting element 160 may be substantially parallel with the longitudinal axis 162. In other examples, the splitting element 160 may be at a fixed or varying angle relative to the longitudinal axis 162 as the splitting element 160 extends between the proximal end 164 and distal end 166 of the tubular sheath 112. For example, as depicted in FIG. 2B, the splitting element 160 may spiral one or more times around the longitudinal axis 162 on the tubular sheath 112 between the proximal end 164 and distal end 166 of the tubular sheath 112. Though the tubular sheath 112 only includes one splitting element 160 as depicted in FIGS. 2A-2C for purposes of clarity, in some examples the tubular sheath 112 may include two or more longitudinal splitting elements 160 at two or more locations around the tubular sheath 112.

In some examples, the inner wall 188 adjacent to the distal end 166 of the tubular sheath 112 may be internally threaded with threads 182. The threads 182 may act as a Luer connector to enable the tubular sheath 112 to connect to an introducer sheath 122. Configuring the inner wall 188 adjacent to the distal end 166 of the tubular sheath 112 to define threads 182 to configure the distal end 166 of the tubular sheath 112 to be a Luer connector may enable the tubular sheath 112 to introduce an expandable balloon 14 to the introducer sheath 122 in a more stable manner. Configuring tubular sheaths 112 to improve the stability of the insertion of expandable balloon 14 may decrease risk of causing physical damage or contact to the expandable balloon 14.

FIG. 2C is a conceptual and schematic diagram illustrating a cross-sectional view along the longitudinal axis 162 of the tubular sheath 112 from the cross-sectional cut plane 174. As depicted in FIG. 2C, the splitting element 160 is within a wall 184 of the tubular sheath 112. In some examples, the splitting element 160 may be entirely between an outer wall 186 of the tubular sheath 112 and an inner wall 188 of the tubular sheath 112. In other examples (not depicted), the splitting element 160 may extend radially in-line with or beyond the outer wall 186 of the tubular sheath 112 (e.g., such that the splitting element 160 partially extends radially beyond a portion of the outer wall 186). In some examples, the tubular sheath 112 may include a space 190 between the splitting element 160 and the inner wall 188 (e.g., such that the splitting element 160 is always at least a minimum radial distance away from the inner wall 188). As a result of the tubular sheath 112 defining the splitting element 160 to always have a space 190 between itself and the inner wall 188, the inner wall 188 may include a relatively smooth longitudinal cross-section, potentially reducing the possibility that an expandable balloon 14 enclosed within the tubular sheath 112 may be damaged by, for example, an internal edge, protrusion, or divot in the inner wall 188.

In some examples, the inner wall 188 may be lubricious to reduce friction between the inner wall 188 and the expandable balloon 14. In some examples, the inner wall 188 may include a lubricious coating, such as a hydrophilic coating, a PTFE coating, a HDPE coating, or the like. For example, the majority of the tubular sheath 112 may be made of LDPE, while the inner wall 188 is coated with a hydrophilic coating, PTFE, or HDPE. Alternatively, the entirety of the tubular sheath 112 may be made of a lubricious material, such as PTFE, HDPE, or the like. Configuring the inner wall 188 of the tubular sheath 112 to be lubricious may reduce the likelihood of the tubular sheath 112 physically damaging an enclosed expandable balloon 14 or removing some of the drug coating on an external surface 48 of an enclosed expandable balloon 14.

The inner wall 188 of the tubular sheath 112 defines an inner lumen 192 of the tubular sheath 112. The inner lumen 192 is configured to enclose the expandable balloon 14. In some examples, cross-sectional dimensions of the inner lumen 192 may be substantially constant along the longitudinal axis 162 of the tubular sheath 112. In other examples, cross-sectional dimensions of the inner lumen 192 as measured along the longitudinal axis 162 of the tubular sheath 112 may vary along a length of the tubular sheath 112.

Though the tubular sheath 112 is discussed and depicted throughout this disclosure as tubular in shape for purposes of clarity and illustration, it is to be understood that many substantially tubular shapes are within the scope of this disclosure. For example, the tubular sheath 112 may define a changing radius 172 along the longitudinal axis 162 of the tubular sheath 112. Additionally or alternatively, the cross-section of the tubular sheath 112 may be, for example, oblong, egg, or diamond-shaped through a portion or the entirety of the length of the tubular sheath 112.

The tubular sheath 112 may be in an enclosing configuration 194 while enclosing the expandable balloon 14 on the catheter 16. The longitudinal splitting element 160 is configured to split open the tubular sheath 112 into a split configuration, such as the split configuration 196 of FIG. 2D. For example, the longitudinal splitting element 160 may include a wire embedded in a wall of the tubular sheath 112 (e.g., similar to the wire 220 in tubular sheath 212A of FIGS. 3A and 3B), such that applying a force to the wire splits the tubular sheath 112 open. For another example, the longitudinal splitting element 160 may include holes and/or grooves that extend through the tubular sheath 112 (e.g., similar to holes 240A-D and grooves 242A-B of tubular sheath 212B of FIGS. 4A and 4B) that structurally weaken the tubular sheath 112, such that a force applied to the holes and/or grooves may result in the tubular sheath 112 splitting along an axis aligned with the holes and/or grooves. When split using the splitting element 160, the tubular sheath 112 may split into the two sides 168, 170 of the tubular sheath 112. The split configuration 196 exposes the inner lumen 192 such that the tubular sheath 112 may be removed from the catheter 16. The tubular sheath 112 may be configured to stay in the enclosing configuration 194 while the expandable balloon 14 is being inserted into the vasculature 24 of a patient 26, as discussed in more detail below.

FIGS. 3A-4B relate to examples of longitudinal splitting elements 160 within example tubular sheaths 212A and 212B (collectively, "tubular sheaths 212"). For example, FIG. 3A is a conceptual and schematic diagram illustrating a side view of an example tubular sheath 212A that includes a longitudinal splitting element 160 including a wire 220. The tubular sheaths 212 may be substantially similar to the tubular sheaths 12 and 112 of FIGS. 1A-2D aside from the differences described herein. For example, the tubular sheaths 212 are not depicted as including a proximal flare 50 or a distal flare 52 for purposes of clarity. In other examples, the tubular sheaths 212 may include both a proximal flare 50 and distal flare 52 as in tubular sheath 12, or the tubular sheaths 212 may have only a proximal flare 50 or only a distal flare 52, or no flare at all. In some examples, the tubular sheath 212 may be relatively easier to split as a result of not including a proximal flare 50 or distal flare 52 (e.g., as a result of a splitting force applied by a physician not having to change angles or directions when applied along the tubular sheath 212). The wire 220 is embedded within a wall 284 of the tubular sheath 212A. The wire 220 may be embedded within the wall 284 substantially similarly to how the longitudinal splitting element 160 was within the wall 184 of the tubular sheath 112.

As depicted in FIG. 3A, the wire 220 may extend substantially parallel with a longitudinal axis 262 of the tubular sheath 212A. A proximal end 222 of the wire 220 may extend proximally from the proximal end 264 of the tubular sheath 212A. Further, a distal end 224 of the wire 220 may extend distally from the distal end 266 of the tubular sheath 212A. In some examples, only one of the proximal end 222 or distal end 224 may extend proximally or distally from respective ends of the tubular sheath 212A, respectively. Configuring the wire 220 to extend from the proximal end 264, distal end 266, or both, of the tubular sheath 212A enables a clinician to apply a force to the wire 220. Tabs 226A-226B (collectively, "tabs 226") may be stably affixed to the proximal end 222 and distal end 224 of the wire 220. The tabs 226 may further facilitate the application of force. In some examples, rather than including both of the tabs 226, the tubular sheath 212A may include only the first tab 226A or only the second tab 226B.

The wire 220 is configured to split the tubular sheath 212A in response to a force above a threshold force being exerted upon the wire 220 (e.g., by a user such as a clinician). To facilitate splitting the tubular sheath 212A, the wire 220 has a substantially higher tensile strength than the tubular sheath 212A through which the wire 220 is pulled. The threshold force may be a force that is higher than a nominal force that may be unintentionally exerted upon the wire 220 while also being less than a maximum force that an adult could exert upon the wire 220. Put differently, the threshold force may be a force that is relatively easy for an adult to intentionally apply to the wire 220 while simultaneously being relatively difficult to unintentionally apply while handling the medical device 10. In some examples, the force may be exerted upon a proximal end 222 or distal end 224 of the wire 220, or exerted upon one of the tabs 226 connected to either end 222, 224 of the wire 220.

Though FIG. 3A depicts a single wire 220 running substantially parallel to the longitudinal axis 262 of the tubular sheath 212A, in other examples, the tubular sheath 212A may include two or more wires 220, each of which may be extending parallel with or at an angle to the longitudinal axis 262 of the tubular sheath 212A. For example, the tubular sheath 212A may include a wire 220 that extends through the wall 284 of the sheath in a spiral about the longitudinal axis 262 (e.g., similar to FIG. 2B).

FIG. 3B is a conceptual and schematic diagram illustrating a cross-sectional view of the tubular sheath 212A and wire 220 of FIG. 3A as viewed facing the cross-sectional cut plane 228. In some examples, the wire 220 may occupy a majority of a cross-sectional thickness 232 of the wall 284 of the tubular sheath 212. For example, a diameter 230 of the wire 220 may be at least 50% of a cross-sectional thickness 232 of the wall 284 of the tubular sheath 212A. In other examples, the wire 220 may be larger (e.g., 75% of the cross-sectional thickness 232) or smaller (e.g., 25% of the cross-sectional thickness 232). Configuring the wire 220 to have a larger diameter may decrease the threshold force needed for a clinician to split the tubular sheath 212A.

Thus, when the tubular sheath 212A is on the expandable balloon 14, the tubular sheath 212A encloses the expandable balloon 14, but once the expandable balloon 14 is inserted into the introducer sheath 22 (FIG. 1A), the wire 220 may be pulled by a clinician or other user in a radially outward direction perpendicular or oblique to the longitudinal axis 262 (for example, in the direction of arrow 229) to split the tubular sheath 212A. Pulling the wire 220 in this manner pulls the wire 220 out of the wall 284, thereby breaking the wall and splitting the tubular sheath 212A into the two sides 268, 270 of the tubular sheath 212A, such that the inner lumen 292 of the tubular sheath 212A is exposed. Once split, the tubular sheath 212A may be removed from the catheter 16 (e.g., in a radial or transverse direction with reference to the longitudinal axis 262 of the tubular sheath 212A). In this way, the tubular sheath 212A including the wire 220 is configured to enclose the expandable balloon 14 until the expandable balloon 14 is inserted into the introducer sheath 22 while also being configured to be splittable, enabling the tubular sheath 212A to be removed from the catheter 16 once the expandable balloon 14 is sufficiently inserted.

FIG. 4A is a conceptual and schematic diagram illustrating a side view of a tubular sheath 212B including a longitudinal splitting element that includes one or more longitudinal holes 240A-240D (collectively, "longitudinal holes 240"). The longitudinal holes 240 may extend from a proximal end 264 of the tubular sheath 212B to a distal end 266 of the tubular sheath 212B. The longitudinal holes 240 may define any shape in cross-section. In some examples, longitudinal holes 240 may define a circular cross-section, which may be more easily manufactured. The longitudinal holes 240 may have a consistent cross-sectional shape along the length of tubular sheath 212B. The longitudinal holes 240 may be formed in the tubular sheath 212B using any suitable technique, such as extrusion or laser cutting. The longitudinal holes 240 may be substantially parallel with the longitudinal axis 262 of the tubular sheath 212B.

In some examples, in addition to the longitudinal holes 240, the tubular sheath 212B may define a longitudinal groove 242 that extends radially in from the outer wall 286 of the tubular sheath 212B. The longitudinal groove 242 may extend from a proximal end 264 of the tubular sheath 212B to a distal end 266 of the tubular sheath 212B. The longitudinal groove 242 may preferably radially align with one or more longitudinal holes 240. Such alignment with the longitudinal groove 242 may facilitate identifying the longitudinal holes 240. For example, where a clinician may have otherwise encountered some difficulty locating the longitudinal holes 240 (e.g., as the longitudinal holes 240 are internal features), the longitudinal groove 242 may provide a readily identifiable external feature to locate the longitudinal holes 240. The longitudinal groove 242 may additionally facilitate more easily splitting the tubular sheath 212B. For example, in some situations the tubular sheath 212B may be sufficiently weakened such that the tubular sheath 212B may be readily split as discussed herein because the tubular sheath 212B includes both the longitudinal holes 240 and the longitudinal groove 242. However, in other examples the longitudinal holes 240 and/or longitudinal groove 242 alone may be sufficient to configure the tubular sheath 212B to be splittable.

In some examples, the tubular sheath 212B may be formed with the longitudinal groove 242. For example, the tubular sheath 212B may be formed using a mold or other tooling (e.g., a nozzle of an extruder) that defines the longitudinal groove 242. In other examples, the longitudinal groove 242 may be formed into the tubular sheath 212B after the tubular sheath 212B is formed using any suitable technique. For example, the longitudinal groove 242 may be longitudinally cut into the tubular sheath 212B using a laser cutter, or the longitudinal groove 242 may be radially cut using a mill or other cutting tool.

Figure 4B:
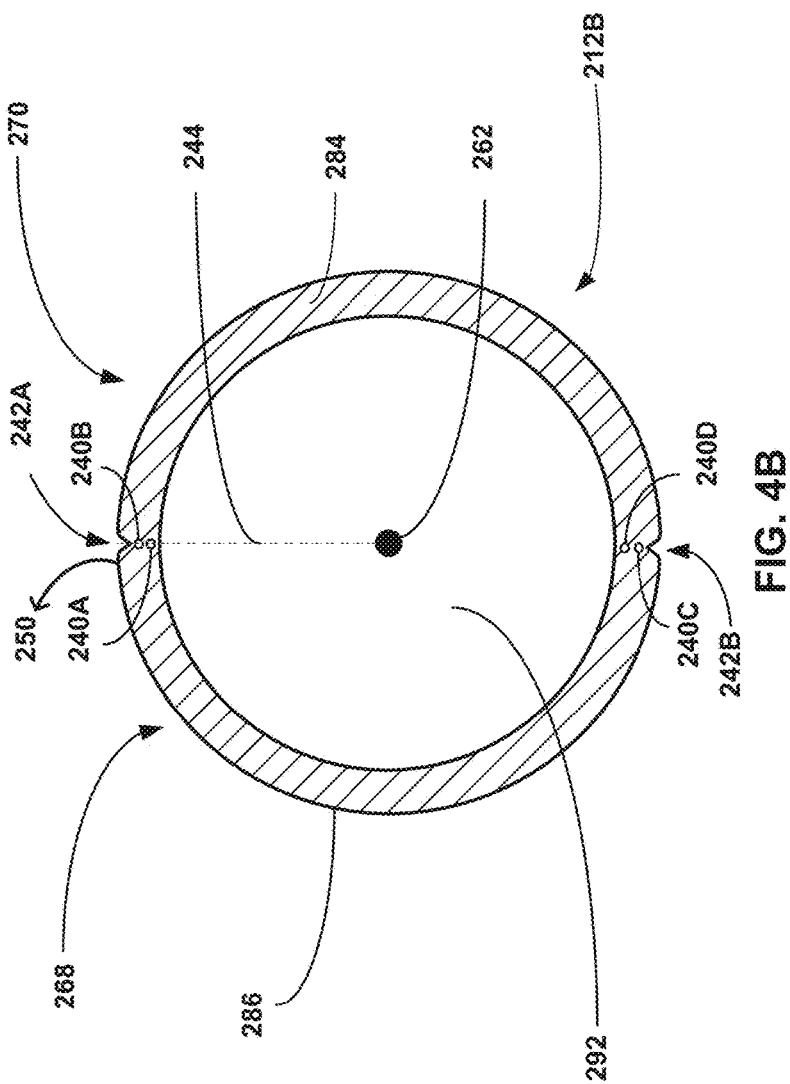

FIG. 4B is a conceptual and schematic diagram illustrating a cross-sectional view of the tubular sheath 212B, the longitudinal holes 240, and the longitudinal grooves 242A, 242B (collectively "longitudinal grooves 242") as viewed at the cross-sectional cut plane 248. Though FIG. 4B depicts four longitudinal holes 240 and two longitudinal grooves 242, other examples may include more or fewer longitudinal holes, more or fewer longitudinal grooves 242, or both. Each longitudinal groove of the longitudinal grooves 242 may be substantially aligned with one or more hole of the longitudinal holes 240.

For example, longitudinal groove 242A is radially aligned with longitudinal holes 240A, 240B, and longitudinal groove 242B is radially aligned with longitudinal holes 240C, 240D. As depicted, the longitudinal groove 242A and longitudinal holes 240A, 240B may all be centered on a radial line 244 that extends radially outward from the longitudinal axis 262 of the tubular sheath 212B. The tubular sheath 212B may define one or more longitudinal holes 240 that are radially in-line with the longitudinal groove 242, such that longitudinal holes 240 are closer to the longitudinal axis 262 of the tubular sheath 212B than the longitudinal groove 242.

Further, in examples in which there are more than one set of longitudinal holes 240 (e.g., more than one radially-aligned set of holes 240 in the tubular sheath 212B) as in longitudinal holes 240A, 240B and longitudinal holes 240C, 240D of FIG. 4A, the sets of longitudinal holes 240 may be arranged evenly throughout the tubular sheath 212B around the circumference of the tubular sheath 212B. For example, if there are two sets of longitudinal holes 240 in the tubular sheath 212B, the two sets of longitudinal holes 240 may be arranged 180° away from each other around the circumference of the tubular sheath 212B, as shown in FIG. 4B. Alternatively, if there were three or four sets of longitudinal holes 240 in the tubular sheath 212B, the three or four sets of longitudinal holes 240 may be arranged 120° or 90° degrees apart around the longitudinal axis 262, respectively. Such a dispersion of multiple sets of longitudinal holes 240 may enable a clinician to more easily split the tubular sheath 212B without having to think about the orientation of the longitudinal holes 240, and thus save procedure time. Additionally, by including a plurality of longitudinal hole 240 sets, the tubular sheath 212B may enable a clinician to select the size of an opening to the inner lumen 292 that would be created upon splitting the tubular sheath 212B (e.g., by selecting different sets of longitudinal holes 240 along which the tubular sheath 212B may be split). By enabling a clinician to select the size of an opening to the inner lumen 292, the tubular sheath 212B may enable a clinician to minimize an amount of contact between the catheter 16 and tubular sheath 212B when the tubular sheath 212B, therein reducing an element of procedural complexity.

The longitudinal holes 240 and the longitudinal grooves 242 are configured to enable the tubular sheath 212B to be split in response to application of a force above a threshold force as discussed herein. For example, a user such as a clinician may apply the force as a shearing or tearing force along the radial line 244. As discussed above, the longitudinal groove 242 may enable a clinician to identify the longitudinal holes 240 and radial line 244 in which the clinician may apply the force. The longitudinal holes 240 and longitudinal groove 242 may define a structurally weak portion of the tubular sheath 212B along the radial line 244 that includes the longitudinal holes 240 and longitudinal groove 242, therein enabling the tubular sheath 212B to be split in response to application of the force above the threshold force by a user. For example, the tubular sheath 212B may be stressed immediately adjacent to the longitudinal holes 240 and longitudinal groove 242, such as in the direction of arrow 250 to create a shearing or tearing force that substantially aligns with the radial line 244 that intersects the longitudinal holes 240 and longitudinal groove 242. The force may be applied using a tab 246 that is attached to the outer wall 286 of the tubular sheath 212B adjacent to the longitudinal groove 242 on the proximal end 264 of the tubular sheath 212B. In other examples, the tab 246 may be located additionally or alternatively on the distal end 266 of the tubular sheath 212B. The tab 246 may be configured to retain a connection to the outer wall 286 in response to a force that greatly exceeds the threshold force, so that the tab 246 may facilitate stressing of the longitudinal holes 240 and longitudinal groove 242 to split the tubular sheath 212B. In other examples, the tubular sheath 212 may include two tabs 246, one on either side of the longitudinal groove 242. In still further examples, the tubular sheath 212B may omit the tab 246 and a clinician or other user may grab the tubular sheath on either side of the longitudinal holes 240.

Thus, when the tubular sheath 212B is on the expandable balloon 14, the tubular sheath 212B encloses at least a portion of the expandable balloon 14, but once the expandable balloon 14 is inserted into a patient 26 (FIG. 1A) a clinician may apply a force radially on the longitudinal groove 242 and/or longitudinal holes 240 to split the tubular sheath 212B. Applying the force radially on the longitudinal holes 240 and or the longitudinal groove 242 splits the tubular sheath 212B into the two sides 268, 270 of the tubular sheath 212B, such that the inner lumen 292 of the tubular sheath 212B is exposed. Once split, a clinician may remove the tubular sheath 212B from the catheter 16 (e.g., in a radially outward or transverse direction). In this way, the tubular sheath 212B with the longitudinal holes 240 and/or the longitudinal groove 242 is configured to enclose the expandable balloon 14 until the expandable balloon 14 is inserted while also being configured to be splittable, enabling the tubular sheath 212B to be removed from the catheter 16 once the expandable balloon 14 is sufficiently inserted.

Alternatively, as discussed above, a tubular sheath 12 may include a gripping portion rather than (or potentially in addition to) a longitudinal splitting element 160. For example, FIGS. 5A-5C are conceptual and schematic diagrams illustrating an example tubular sheath 312, including a side view (FIG. 5A), a cross-sectional view taken along line 374 (FIG. 5B), and a side view in an open configuration (FIG. 5C). The tubular sheath 312 may be substantially similar to the tubular sheaths 12 and 112 of FIGS. 1A-2D, aside from the differences described herein.

The tubular sheath 312 may include a gripping portion 350. The gripping portion 350 may be a section of the wall of the tubular sheath that extends from a proximal end 364 of the tubular sheath 312 to a distal end 366 of the tubular sheath 312 and is configured to be pulled away and out from the tubular sheath to split open the tubular sheath 312. The gripping portion 350 is configured to have relatively poor cohesive strength to adjacent portion 378, 380 of the tubular sheath 312. For example, the gripping portion 350 may be lined with a plurality of perforations (e.g., similar to the tubular sheath 412A of FIGS. 6A and 6B as described below). In such examples, the gripping portion 350 may have relatively poor cohesive strength to adjacent portions 378, 380 as a result the perforations that divide the gripping portion 350 from the adjacent portions 378, 380. For another example, the gripping portion 350 may be made of a different material than the tubular sheath 312 (e.g., similar to the tubular sheath 412B of FIGS. 7A and 7B as described below). In such an example, the two materials will bond to each other to provide a closed tubular sheath 312, but the bond strength will be such that a sufficient force will break the bond. In one such example, the tubular sheath 312 may be made of HDPE, while the gripping portion 350 may be made of PEBAX® (thermoplastic elastomers available from Arkema, Colombes, France), which does not bond strongly to HDPE. In another example, the gripping portion 350 may be attached to the tubular sheath 312 in such a way as to produce a weak bond, such as an ultrasonic weld at a relatively suboptimum frequency, a chemical bond with a relatively weak adhesive, a solvent bond using a solvent that will soften the materials without producing a relatively strong bond, or co-extruding the gripping portion 350 and the tubular sheath 312 at a relatively suboptimum temperature. As depicted in FIG. 5A, the gripping portion 350 may be substantially parallel with a longitudinal axis 362 of the tubular sheath 312. In other examples, the gripping portion 350 may be at a fixed or varying angle relative to the longitudinal axis 362 as the gripping portion 350 extends between the proximal end 364 and distal end 366 of the tubular sheath 312 (e.g., similar to how the longitudinal splitting element 160 spirals around the tubular sheath 212 in FIG. 2B).

It is to be understood that the depicted amount of the tubular sheath 312 that includes the gripping portion 350 within FIG. 5A and 5B is for purposes of illustration only. In other examples, the gripping portion 350 may include more or less of the tubular sheath 312. The amount of the tubular sheath 312 that includes the gripping portion 350 is configured to enable the grasping and pulling of the gripping portion 350 away from the tubular sheath 312. As such, it may be advantageous to configure the gripping portion 350 to include a relatively small amount (e.g., less than 45%) of the tubular sheath 312 to facilitate such grasping and pulling.

As depicted in FIG. 5B, the gripping portion 350 may extend from an inner wall 388 of the tubular sheath 312 to an outer wall 386 of the tubular sheath 312. The gripping portion 350 may extend from the outer wall 386 to the inner wall 388 for the majority or the entirety of the length of the tubular sheath 312. As depicted in FIG. 5B, perimeter walls 352A, 352B (collectively, "perimeter walls 352) of the gripping portion 350 may extend radially straight in towards the longitudinal axis 362 of the tubular sheath 312. In other examples, the perimeter walls 352 of the gripping portion 350 may extend from the outer wall 386 to the inner wall 388 at an angle other than substantially straight radially inwards towards the longitudinal axis 362 to create a more acute or obtuse angle with the inner wall 388. The angles of the perimeter walls 352 may impact an amount of cohesive strength that the gripping portion 350 has to the adjacent portions 378, 380. For example, if the perimeter walls 352 extend to the inner wall 388 with a relatively acute angle, the gripping portion 350 may have relatively less cohesive strength to adjacent portions 378, 380 (e.g., such that it is relatively easier to pull the gripping portion 350 from tubular sheath 312), whereas if the perimeter walls 352 extend to the inner wall 388 with a relatively obtuse angle, the gripping portion 350 may have relatively more cohesive strength to adjacent portions 378, 380 (e.g., such that it is relatively harder to pull the gripping portion 350 from tubular sheath 312).

The tubular sheath 312 is in an enclosing configuration 394 while enclosing the expandable balloon 14 on the catheter 16. The gripping portion 350 is configured to split open the tubular sheath 312 into a split configuration, such as the split configuration 396 of FIG. 5C. To split the tubular sheath 312, a user such as a clinician may hold the gripping portion 350 and pull it radially away from the tubular sheath 312, such as along arrow 355. When split using the gripping portion 350, the tubular sheath 312 may split along the adjacent portions 378, 380, with the gripping portion 350 being substantially removed from the tubular sheath 312, or the tubular sheath 312 may split along only one of the adjacent portions 378, 380. The split configuration 396 exposes the inner lumen 392 such that the tubular sheath 312 may be removed from the catheter 16. The tubular sheath 312 is configured to stay in the enclosing configuration 394 while the expandable balloon 14 is being inserted into the vasculature 24 of a patient 26 (FIG. 1A), as discussed herein.

Figure 6A:
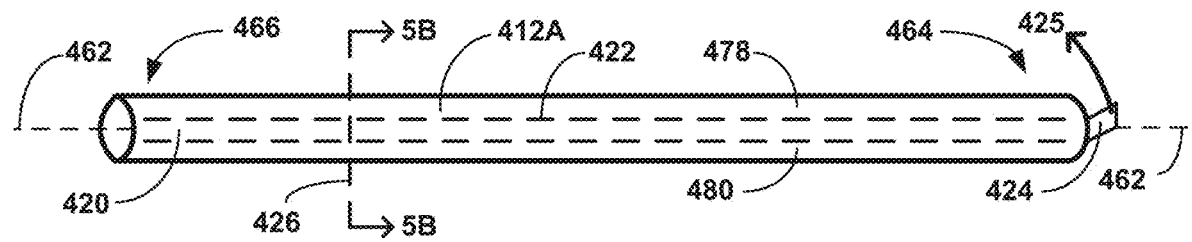
FIGS. 6A and 6B are conceptual and schematic diagrams illustrating a side view of a tubular sheath with a second example gripping portion (FIG. 6A) and a cross-sectional view of the tubular sheath of FIG. 6A taken along cross-sectional cut plane 426 (FIG. 6B).

FIGS. 6A-7B relate to tubular sheaths 412A, 412B (collectively, "tubular sheaths 412") that include gripping portions 350. The tubular sheaths 412 may be substantially similar to the tubular sheath 12, 112, 212, 312 of FIGS. 1A-5C aside from the differences described herein. FIG. 6A is a conceptual and schematic diagram illustrating a side view of a tubular sheath 412A that includes an example perforated gripping portion 420. The perforated gripping portion 420 may be a longitudinal segment or portion of the tubular sheath 412A that is perforated to facilitate the perforated gripping portion 420 being pulled out from the tubular sheath 412A, such as in the direction of arrow 425. The perforated gripping portion 420 may extend from a proximal end 464 of the tubular sheath 412A to a distal end 466 of the tubular sheath 412A. In some examples, the perforated gripping portion 420 may extend through the tubular sheath 412A substantially parallel with the longitudinal axis 462 of the tubular sheath 412A. In other examples (not depicted), the perforated gripping portion 420 may extend through the tubular sheath 412A at an angle to or in a spiral around the longitudinal axis 462 on the tubular sheath 412A (e.g., similar to FIG. 2B).

The perforated gripping portion 420 may have a relatively poor cohesive strength to adjacent portion 478, 480 of the tubular sheath 412A as a result of a plurality of perforations 422. The plurality of perforations 422 may extend from the proximal end 464 of the tubular sheath 412A to the distal end 466 of the tubular sheath 412A. The plurality of perforations 422 may be located at the nexuses between the perforated gripping portion 420 and the adjacent portions 478, 480 of the tubular sheath 412A. The length of and spacing between perforations 422 depicted in FIG. 6A is for purposes of illustration only; other lengths and spaces between perforations 422 that result in the configurations discussed herein are also possible. Each perforation 422 may cut substantially through one side of the tubular sheath 412A. In some examples, the tubular sheath 412A is constructed as a unitary structure without perforations 422, such that the perforations 422 are radially cut into the tubular sheath 412 post-construction to define the perforated gripping portion 420. The plurality of perforations 422 enable the perforated gripping portion 420 to be pulled out (e.g., removed) from the tubular sheath 412A in response to a force (e.g., arrow 425) above a threshold force as discussed herein. Pulling the perforated gripping portion 420 from the tubular sheath 412A result in the tubular sheath 412A being split, such that the tubular sheath 412A may be removed from the catheter 16.

In some examples, the perforated gripping portion 420 may include a tab 424 upon which the force above the threshold force may be applied. The tab 424 may extend proximally from the proximal end 464 of the tubular sheath 412A. In other examples, a tab 424 may alternatively or additionally extend distally from the distal end 466 of the tubular sheath 412A. The tab 424 may have a relatively strong cohesive bond to, or be formed integrally with, the perforated gripping portion 420, such that the tab 424 may remain securely attached to the perforated gripping portion 420 in response to a force far greater than the threshold force, so that the tab 424 is configured to remain attached to the perforated gripping portion 420 when the force greater than the threshold force is applied to the tab 424. In some examples, the tubular sheath 412A may omit the tab 424 and a user such as a clinician may apply the force directly to the perforated gripping portion 420.

Figure 6B:
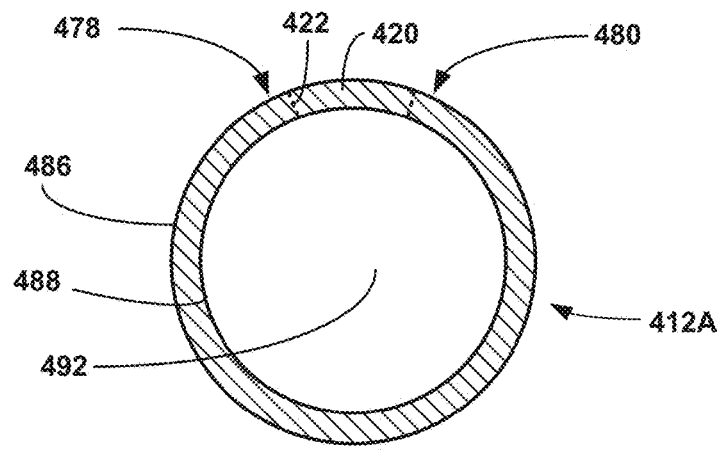

FIG. 6B is a conceptual and schematic diagram illustrating a cross-sectional view of the tubular sheath 412A of FIG. 6A as viewed facing the cross-sectional cut-plane 426. As depicted in FIG. 6B, the perforations 422 extend radially from an inner surface 488 of the tubular sheath 412A to an outer surface 486 of the tubular sheath 412A. A user applying the force above the threshold force to the incongruous gripping portion 440 results in the tubular sheath 412A splitting open such that the inner lumen 492 is exposed.

Thus, when the tubular sheath 412A is around the expandable balloon 14, the tubular sheath 412A encloses at least a portion of the expandable balloon 14, but once the expandable balloon 14 is inserted, a user may apply the force to the perforated gripping portion 420 (e.g., using a tab 424) to split the tubular sheath 412A. As a result of a user applying the force to the perforated gripping portion 420 in an outward radial direction (e.g., relative to the tubular sheath 412A), such as along arrow 425, the tubular sheath 412A may split between the two portions 478, 480 of the tubular sheath 412A, such that the inner lumen 492 of the tubular sheath 412A is exposed. Once split, a user may remove the tubular sheath 412A from the catheter 16 (e.g., in a radially outward or transverse direction). In this way, the tubular sheath 412A with the perforated gripping portion 420 is configured to enclose the expandable balloon 14 until the expandable balloon 14 is inserted into the introducer sheath while also being configured to be splittable, enabling the tubular sheath 412A to be removed from the catheter 16 once the expandable balloon 14 is sufficiently inserted.

Figure 7A:
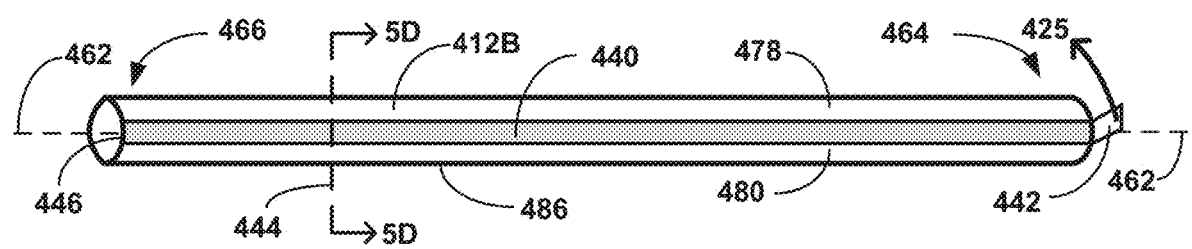
FIGS. 7A and 7B are conceptual and schematic diagrams illustrating a side view of a tubular sheath with a third example gripping portion (FIG. 7A) and a cross-sectional view of the tubular sheath of FIG. 7A taken along cross-sectional cut plane 444 (FIG. 7B).

FIG. 7A is a conceptual and schematic diagram illustrating a side view of an example tubular sheath 412B with yet another example gripping portion 350. The gripping portion 350 of FIG. 7A may be an incongruous gripping portion 440 that is made from a different material than the rest of the tubular sheath 412B. The incongruous gripping portion 440 may extend from a proximal end 464 of the tubular sheath 412B to a distal end 466 of the tubular sheath 412B. In some examples, the incongruous gripping portion 440 may longitudinally extend along the tubular sheath 412B substantially in parallel with the longitudinal axis 462 of the tubular sheath 412B. In other examples (not depicted), the incongruous gripping portion 440 may extend through the tubular sheath 412B at an angle to or even in a spiral around the longitudinal axis 462 on the tubular sheath 412B.

The incongruous gripping portion 440 may have a relatively poor cohesive strength to adjacent portions 268, 270 of the tubular sheath 412B. The relatively poor cohesive strength may be a result of the incongruous gripping portion 440 including a first material and the adjacent portions 478, 480 of the tubular sheath 412B including a second material. In some examples, the first material and second material may have a relatively poor bond to each other (e.g., the first material is HDPE and the second material is pebax or nylon), such that the first material would pull away from the second material in response to a force greater than the threshold force as discussed herein. Alternatively, the first material may have a greater density and/or tensile strength than the second material (e.g., the first material is HDPE and the second material is LDPE), such that the first material tears or breaks before the second material in response to the force greater than the threshold force as discussed herein. The tubular sheath 412B may be constructed in a single operation. For example, the incongruous gripping portion 440 and the adjacent portions 478, 480 may be co-extruded using two different materials as described above, such that the tubular sheath 412B, including the incongruous gripping portion 440, is fully constructed after the single extrusion process.

In certain examples, the incongruous gripping portion 440 may include a tab 442 attached to the incongruous gripping portion 440 at the proximal end 464 of the tubular sheath 412B. The tab 442 may be configured to facilitate the removal of the incongruous gripping portion 440 from the tubular sheath 412B. In other examples, a tab 442 may alternatively or additionally be connected to the incongruous gripping portion 440 at the distal end 466 of the tubular sheath 412B.

Figure 7B:
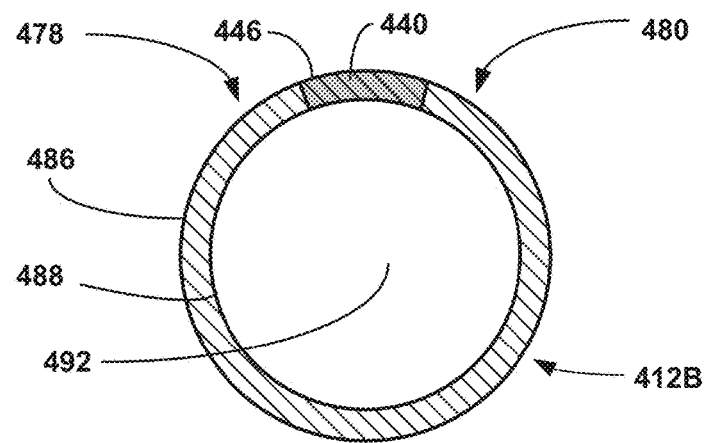

FIG. 7B is a conceptual and schematic diagram illustrating a cross-sectional view of the tubular sheath 412B of FIG. 7B taken along cross-sectional cut-plane 444. As depicted in FIG. 7B, the incongruous gripping portion 440 may extend radially from an inner surface 488 of the tubular sheath 412B to an outer surface 486 of the tubular sheath 412B. In some examples, the incongruous gripping portion 440 may have a different appearance (e.g., be colored differently, textured differently, have a different opacity, or the like) than the rest of the tubular sheath 412B. Forming the incongruous gripping portion 440 with a different appearance relative to the rest of the tubular sheath 412B may provide benefits in identifying the incongruous gripping portion 440. In some examples, the entirety of the tubular sheath 412B may define a different appearance than the incongruous gripping portion 440, as depicted in FIG. 7B. In other examples, only an outer surface 446 of the incongruous gripping portion 440 may be a different appearance than an outer surface 486 of the tubular sheath 412B.

Thus, when the tubular sheath 412B is on the expandable balloon 14, the tubular sheath 412B encloses at least a portion of the expandable balloon 14, but once the expandable balloon 14 is inserted into the introducer sheath 22 a clinician may apply a force to the incongruous gripping portion 440 (e.g., using a tab 442) to split the tubular sheath 412B. Applying the force to the incongruous gripping portion 440 radially away from the tubular sheath 412B, such as shown by arrow 455, splits the tubular sheath 412B between the two portions 478, 480 of the tubular sheath 412B, such that the inner lumen 492 of the tubular sheath 412B is exposed. Once split, the tubular sheath 412B may be removed from the catheter 16 (e.g., in a radially outward or transverse direction). In this way, the tubular sheath 412B with the incongruous gripping portion 440 is configured to enclose the expandable balloon 14 until the expandable balloon 14 is inserted into the introducer sheath 22 while also being configured to be splittable, enabling the tubular sheath 412B to be removed from the catheter 16 once the expandable balloon 14 is sufficiently inserted.

Figure 8:
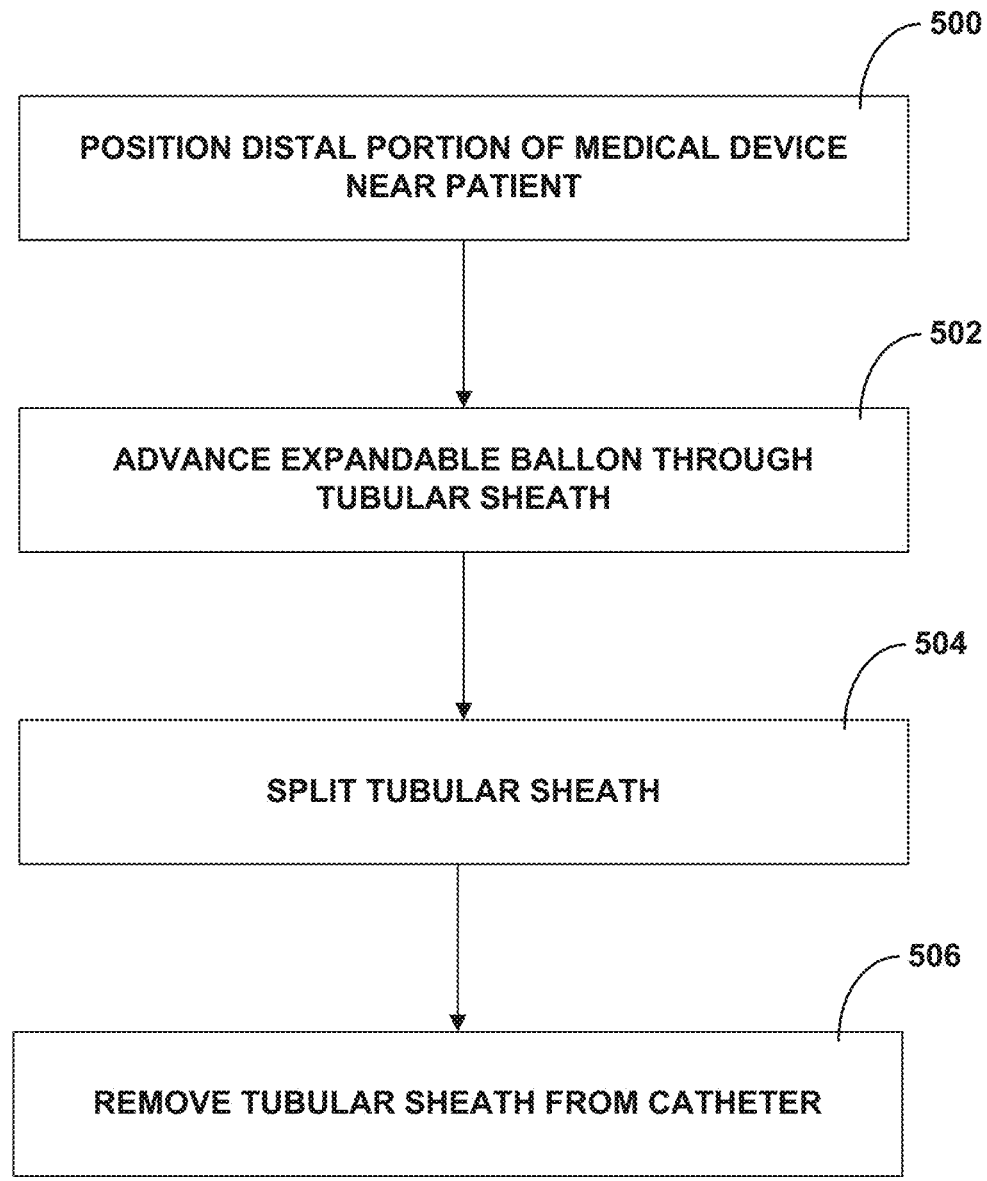
FIG. 8 is a flow diagram illustrating an example method of inserting an expandable balloon into a patient using a tubular sheath of the present disclosure.

FIG. 8 is a flow diagram illustrating an example method of inserting expandable balloons 14 using tubular sheaths 12. Although FIG. 8 will be described with reference to the medical device 10 and other components illustrated in FIGS. 1A-ID, it will be appreciated that the technique of FIG. 8 may be used with any of the medical devices described herein. The flow diagram of FIG. 8 is discussed in conjunction with FIGS. 9A-9C for purposes of clarity.

A clinician may position a distal portion 18 of a medical device 10 near a patient 26 (500). In some examples, the clinician may position the distal portion 18 of the medical device 10 near an introducer sheath 22 that is inserted within the patient 26. The clinician may distally move the catheter 16, expandable balloon 14, and the tubular sheath 12 in conjunction as the distal portion 18 is positioned near the introducer sheath 22. The introducer sheath 22 may terminate in vasculature 24 of the patient 26. The clinician may position/guide the distal portion 18 of the medical device 10 near the introducer sheath 22 using a guidewire 20 that extends proximally from the introducer sheath 22. For example, the clinician may insert the guidewire 20 into the guidewire lumen 42 of the catheter 16.

Figure 9A:
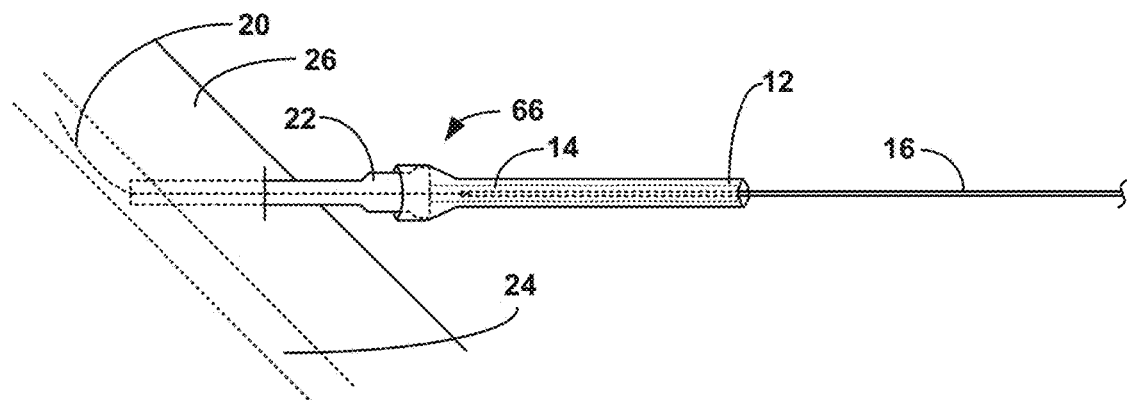
FIGS. 9A-9C are conceptual and schematic diagrams illustrating an example tubular sheath of the present disclosure being inserted according to the flow diagram of FIG. 8, including the example tubular sheath of the present disclosure being located proximal to an example introducer sheath (FIG. 9A), being pushed proximally by the example introducer sheath (FIG. 9B), and being split open on the example catheter (FIG. 9C), respectively.

In FIG. 9A, a clinician mates the distal end 66 of the tubular sheath 12 with the introducer sheath 22. The tubular sheath 12 may stably receive or be stably received by the introducer sheath 22 (e.g., using a Luer connection) to ensure a solid transfer of the expandable balloon 14. In some examples, the distal end 66 of the tubular sheath 12 may act as a Luer connector that engages a Luer connection of the introducer sheath 22 (e.g., internal threads 182 of the tubular sheath 12 may be threaded onto threads 23 of the introducer sheath 22 as the introducer sheath 22 is received by the tubular sheath 12).

Figure 9B:
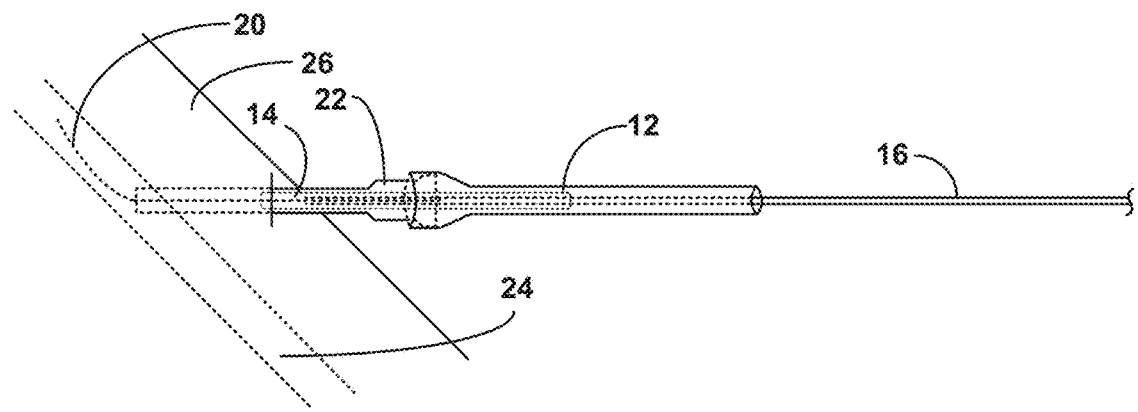

The clinician may push the expandable balloon 14 through the tubular sheath 12 into the introducer sheath 22 (502). The clinician may push the expandable balloon 14 into the introducer sheath 22 by distally pushing the catheter 16 and/or catheter 16 hub 38. The clinician may advance the expandable balloon 14 and catheter 16 over the guidewire 20 into the introducer sheath 22 while the tubular sheath 12 remains stationary (e.g., stationary relative to the catheter 16 and expandable balloon 14) as depicted in FIG. 9B. In some examples, the clinician may advance the expandable balloon 14 and catheter 16 in response to the tubular sheath 12 being stably received by the introducer sheath 22 (e.g., using a Luer connection). In this way, the clinician may insert the expandable balloon 14 into the introducer sheath 22 and therein introduce the expandable balloon 14 to the vasculature 24 of a patient 26 without manually handling or otherwise having an external surface 48 of the expandable balloon 14 contacted in a notable manner. The tubular sheath 12 thus is configured to avoid substantially all contact with the expandable balloon 14 while the expandable balloon is being inserted.

Once the expandable balloon 14 is entirely within the introducer sheath 22/patient 26/vasculature 24, the clinician may slide the tubular sheath 12 proximally on the catheter 16. The catheter 16 remains substantially stationary while the clinician slides the tubular sheath 12 proximally along the catheter 16. In some examples, the clinician may slide the tubular sheath 12 proximally up to the hub 38 of the catheter 16.

Figure 9C:
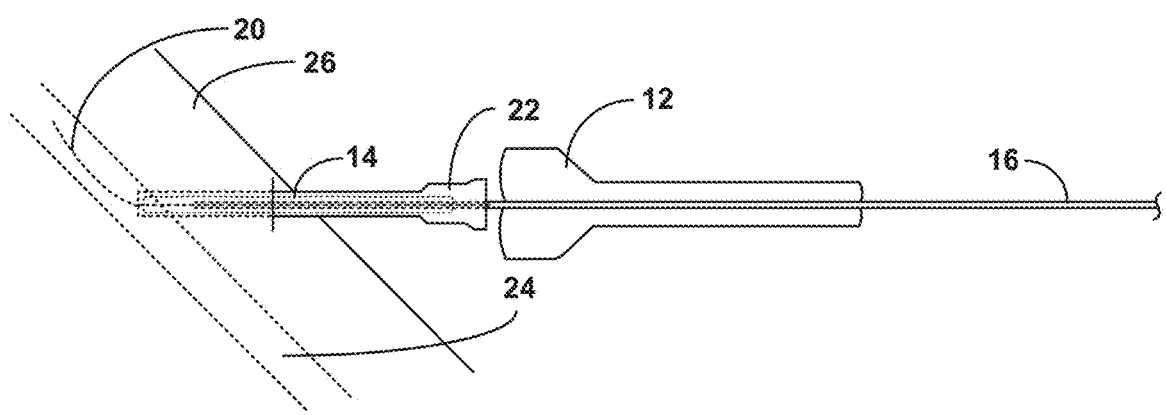

As shown in FIG. 9C, the clinician then splits open the tubular sheath 12 (504). In some example procedures, the clinician may split open the tubular sheath 12 in response to fully inserting the expandable balloon 14 into the introducer sheath 22 and proximally sliding the tubular sheath 12.

The clinician may remove the tubular sheath 12 by converting the tubular sheath 12 into an open configuration by splitting the tubular sheath 12 open using a longitudinal splitting element 160 or gripping portion 350. In some examples, the clinician splits open the tubular sheath 12 by applying a force greater than a threshold force to a longitudinal splitting element 160 within the wall 184 of the tubular sheath, as explained above with reference to the various examples. In other examples, the clinician splits the tubular sheath 12 by applying a force greater than a threshold force upon a gripping portion 350 of the tubular sheath 12 that has poor cohesive strength to adjacent portions 378, 380 of the tubular sheath 12, as explained above with reference to the various examples. The clinician splits the tubular sheath 12 to expose the inner lumen 192 of the tubular sheath 12 (i.e., converting the tubular sheath 12 into an open configuration). Upon exposing the inner lumen 192 of the tubular sheath 12, the clinician may remove the tubular sheath 12 from the catheter 16 (506).

Various examples of the disclosure have been described. These and other examples are within the scope of the following claims.

What is claimed is:
1. A medical device comprising:
a catheter configured to be navigated through vasculature of a patient, the catheter comprising a distal portion and a proximal portion;
an expandable balloon that is attached to the distal portion of the catheter;
a tubular sheath comprising a proximal end and a distal end,
wherein the tubular sheath defines a groove extending longitudinally from the proximal end to the distal end, the groove configured to split the tubular sheath from the proximal end to the distal end in response to application of a force above a threshold force, wherein the tubular sheath defines a radius from a longitudinal axis of the tubular sheath, and wherein the tubular sheath is configured to separate from the catheter in a radial direction defined by the radius when the groove splits the tubular sheath from the proximal end to the distal end; and an introducer sheath configured to be inserted into the vasculature, wherein the introducer sheath is configured to allow the expandable balloon and the catheter to pass through the introducer sheath and stop the tubular sheath from passing through the introducer sheath, and wherein at least one of:

the introducer sheath is configured to threadably engage the tubular sheath, the introducer sheath defines a proximal internal diameter configured to allow the tubular sheath to insert distal to the proximal internal diameter and defines a distal internal diameter distal to and less than the proximal internal diameter, wherein the distal internal diameter is configured to prevent the tubular sheath from inserting distal to the distal internal diameter, or the tubular sheath defines a distal inner diameter configured to allow the introducer sheath to insert proximally into an inner lumen defined by the tubular sheath and defines a proximal inner diameter proximal to and less than the distal inner diameter, wherein the proximal inner diameter is configured to prevent the introducer sheath from inserting within the tubular sheath proximal to the proximal inner diameter.

2. The medical device of claim 1, wherein the tubular sheath defines a hole extending longitudinally through a wall of the tubular sheath, wherein the wall completely surrounds a cross-section defined by the hole.

3. The medical device of claim 2, wherein the groove is radially in-line with the hole.

4. The medical device of claim 1, further comprising a gripping portion attached to an outer wall of the tubular sheath, the gripping portion configured to remain attached to the outer wall in response to a force that exceeds the threshold force.

5. The medical device of claim 4, wherein the gripping portion is a first tab and the medical device further comprising a second tab attached to the outer wall of the tubular sheath, wherein the groove is between the first tab and the second tab.

6. The medical device of claim 1, wherein the groove is substantially parallel to the longitudinal axis.

7. The medical device of claim 1, wherein the groove spirals around the longitudinal axis.

8. The medical device of claim 1, wherein the groove defines a first side of the tubular sheath and a second side of the tubular sheath, and wherein the groove is configured to split the tubular sheath between the first side and the second side.

9. The medical device of claim 1, wherein the tubular sheath comprises at least one of poly (tetrafluoroethylene), high density polyethylene, or low density polyethylene.

10. The medical device of claim 1, wherein a length of the tubular sheath along the longitudinal axis is greater than a length of the expandable balloon along a longitudinal axis of the expandable balloon in the deflated state.

11. The medical device of claim 1, wherein the tubular sheath is configured to remain stationary relative to the introducer sheath while sliding proximally relative to the catheter when the introducer sheath mates with the distal end.

12. A method of inserting expandable balloons, the method comprising:
locating a distal portion of a catheter of a medical device immediately proximal to an introducer sheath inserted in vasculature of a patient, the medical device comprising:
an expandable balloon that is attached to the distal portion of the catheter, and
a tubular sheath comprising a proximal end and a distal end, wherein the tubular sheath is configured to enclose the expandable balloon, and wherein the tubular sheath defines a groove extending longitudinally from the proximal end to the distal end, the groove configured to split the tubular sheath from the proximal end to the distal end in response to application of a force above a threshold force;
distally pushing the catheter toward an introducer sheath and causing the introducer to mate with the tubular sheath to stop the tubular sheath from passing through the introducer sheath into the vasculature when the expandable balloon and the catheter pass through the introducer sheath into the vasculature, wherein causing the introducer sheath to mate with the tubular sheath comprises at least one of:
threadably engaging, by the introducer sheath, the introducer sheath and the tubular sheath,
receiving, by the introducer sheath, the tubular sheath by inserting the tubular sheath distal to a proximal internal diameter defined by the introducer sheath and preventing, using a distal internal diameter of the introducer sheath, the tubular sheath from inserting distal to the distal internal diameter, wherein the distal internal diameter is distal to and less than the proximal internal diameter, or
receiving, by the tubular sheath, the introducer sheath by inserting the introducer sheath proximal to a distal inner diameter defined by the tubular sheath and preventing, using a proximal inner diameter of the tubular sheath, the introducer sheath from inserting within the tubular sheath and proximal to the proximal inner diameter, wherein the proximal inner diameter is proximal to and less than the distal inner diameter; and
splitting the tubular sheath by applying the force above the threshold force to remove the tubular sheath from the catheter when the expandable balloon is fully inserted in the introducer sheath.

13. The method of claim 12, further comprising distally pushing the catheter into the introducer sheath without substantial contact between the tubular sheath and the expandable balloon.

14. The method of claim 12, wherein splitting the tubular sheath comprises applying the force above the threshold force to a tab attached to an outer wall of the tubular sheath.

15. A medical device comprising:
a catheter configured to be navigated through vasculature of a patient, the catheter comprising a distal portion and a proximal portion;
an expandable balloon that is attached to the distal portion of the catheter; and
a tubular sheath comprising a proximal end and a distal end,
wherein the tubular sheath defines a structural feature configured to split the tubular sheath from the proximal end to the distal end in response to application of a force above a threshold force; and an introducer sheath configured to be inserted into the vasculature, wherein the introducer sheath is configured to allow the expandable balloon and the catheter to pass through the introducer sheath and stop the tubular sheath from passing through the introducer sheath, and wherein at least one of:

the introducer sheath is configured to threadably engage the tubular sheath, the introducer sheath defines a proximal internal diameter configured to allow the tubular sheath to insert distal to the proximal internal diameter and defines a distal internal diameter distal to and less than the proximal internal diameter, wherein the distal internal diameter is configured to prevent the tubular sheath from inserting distal to the distal internal diameter, or the tubular sheath defines a distal inner diameter configured to allow the introducer sheath to insert proximally into an inner lumen defined by the tubular sheath and defines a proximal inner diameter proximal to and less than the distal inner diameter, wherein the proximal inner diameter is configured to prevent the introducer sheath from inserting within the tubular sheath and proximal to the proximal inner diameter.

16. The method of claim 12, wherein splitting the tubular sheath enables separation of the tubular sheath from the catheter in a radial direction defined by a radius, the radius defined by the tubular sheath.

17. The medical device of claim 1, wherein the groove extends radially inward from an outer wall of the tubular sheath.

18. The medical device of claim 15, wherein the structural feature comprises at least one of:

a groove extending longitudinally from the proximal end to the distal end, or a hole extending longitudinally through a wall of the tubular sheath.

19. The medical device of claim 15, wherein the structural feature defines a first side of the tubular sheath and a second side of the tubular sheath, and wherein the structural feature is configured to split the tubular sheath between the first side and the second side.

20. The medical device of claim 15, wherein the structural feature includes a first hole extending longitudinally through a wall of the tubular sheath and a second hole extending longitudinally through the wall of the tubular sheath, wherein the first hole and the second hole are dispersed from each other around a circumference of the tubular sheath.

* * * * *